US008138143B2

(12) United States Patent
Fallon et al.

(10) Patent No.: US 8,138,143 B2
(45) Date of Patent: *Mar. 20, 2012

(54) METHODS FOR TREATING A NEUROLOGICAL DISORDER BY PERIPHERAL ADMINISTRATION OF A TROPHIC FACTOR

(75) Inventors: James H. Fallon, Irvine, CA (US); Richard M. Kinyamu, Irvine, CA (US)

(73) Assignee: Neurorepair, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/869,486

(22) Filed: Aug. 26, 2010

(65) Prior Publication Data

US 2011/0105395 A1 May 5, 2011

Related U.S. Application Data

(63) Continuation of application No. 10/167,384, filed on Jun. 10, 2002, now Pat. No. 7,795,202, which is a continuation-in-part of application No. 09/129,028, filed on Aug. 4, 1998, now Pat. No. 7,790,669.

(60) Provisional application No. 60/055,383, filed on Aug. 4, 1997, provisional application No. 60/328,725, filed on Oct. 11, 2001, provisional application No. 60/297,518, filed on Jun. 11, 2001.

(51) Int. Cl.
*A61K 38/00* (2006.01)
*A61K 49/00* (2006.01)
*A61K 38/18* (2006.01)
*A61B 5/00* (2006.01)
*C07K 14/475* (2006.01)
*C07K 14/48* (2006.01)

(52) U.S. Cl. ............ 514/1.1; 514/1.2; 514/1.3; 514/7.6; 514/8.3; 514/8.4; 424/9.1

(58) Field of Classification Search ........................ None
See application file for complete search history.

(56) References Cited

U.S. PATENT DOCUMENTS

| | | | |
|---|---|---|---|
| 4,816,561 A | 3/1989 | Todaro | |
| 4,863,899 A | 9/1989 | Todaro | |
| 4,863,902 A | 9/1989 | Amagase et al. | |
| 5,026,381 A | 6/1991 | Li | |
| 5,240,912 A | 8/1993 | Todaro | |
| 5,342,777 A | 8/1994 | Cole et al. | |
| 5,411,883 A | 5/1995 | Boss et al. | |
| 5,750,376 A | 5/1998 | Weiss et al. | |
| 5,756,457 A | 5/1998 | Wang et al. | |
| 5,800,812 A | 9/1998 | Eisenbach-Schwartz et al. | |
| 5,851,832 A | 12/1998 | Weiss et al. | |
| 5,942,487 A | 8/1999 | Ogawa et al. | |
| 5,980,885 A | 11/1999 | Weiss et al. | |
| 5,981,165 A | 11/1999 | Weiss et al. | |
| 6,071,889 A | 6/2000 | Weiss et al. | |
| 6,093,531 A | 7/2000 | Bjornson et al. | |
| 6,486,122 B1 | 11/2002 | Twardzik et al. | |
| 6,677,307 B2 | 1/2004 | Twardzik et al. | |
| 6,764,683 B1 | 7/2004 | Twardzik et al. | |
| 6,815,418 B2 | 11/2004 | Twardzik et al. | |
| 7,329,645 B2 | 2/2008 | Twardzik et al. | |
| 7,365,172 B2 | 4/2008 | Twardzik et al. | |
| 7,795,202 B2 * | 9/2010 | Fallon et al. ................... | 514/8.9 |
| 2001/0007657 A1 * | 7/2001 | Reid et al. .................... | 424/93.7 |
| 2002/0193301 A1 | 12/2002 | Twardzik et al. | |
| 2008/0242611 A1 | 10/2008 | Twardzik et al. | |
| 2009/0068139 A1 | 3/2009 | Twardzik et al. | |

FOREIGN PATENT DOCUMENTS

| | | |
|---|---|---|
| WO | WO 93/01275 | 1/1993 |
| WO | WO 94/16718 | 8/1994 |
| WO | WO 98/22127 | 5/1998 |
| WO | WO 99/06060 | 2/1999 |
| WO | WO 00/65028 | 11/2000 |
| WO | WO 01/12127 | 2/2001 |

OTHER PUBLICATIONS

Abboud, et al., "Insulin Effects on Differentiation of Fetal Neuron Cell Cultures," Soc . Neurosci. Abstr. 23 : 1425, 1997.
"Adult stem cells activated in mammalian brain", http://today.uci.edu/news/release_detail.asp?key=1801, Jul. 24, 2008.
Ahmed S., et al., "BDNF Enhances the Differentiation but not the Survival of CNS Stem Cell-Derived Neuronal Precursors" Journal of Neuroscience, New York, NY, US vol. 15, No. 8, Aug. 1, 1995 pp. 5765-5778.
Alexi T., et al., "Protective Effects of Neurotrophin-4/5 and Transforming Growth Factor-α on Striatal Neuronal Phenotypic Degeneration After Excitotoxic Lesioning With Quinolinic Acid" (1997) Neuroscience 78(1):73-86.
Alexi T., et al.,"Trophic Actions of Transforming Growth Factor A on Mesencephalic Dopaminergic Neurons Developing in Culture" (1993) Neuroscience 55(4):903-918.
Alheid, et al., "Theories of basal forebrain organization and the "emotional motor system"," Progr. Brain Res. 107:461-484, 1996.
Anchan et al., "EGF and TGF-α Stimulate Retinal Neuroepithelial Cell Proliferation In Vitro," Neuron, 6: 923-936 (1991).
Andersson, et al., "Differential Expression of Fgfri—R4 in the Rat Nervous System", Dept. Cell Biology & Anatomy, Oregon Health Services University, Portland, OR 97201, Society for Neuroscience Abstracts vol. 20, 1994, p. 40.
Babic, et al., "CYR61, a product of a growth factor-inducible immediate early gene, promotes angiogenesis and tumor growth," Proc. NatL Acad. Sci. USA, 95:6355, 1998.
Barnard, et al., "Auto- and Cross-induction within the Mammalian Epidermal Growth Factor-related Peptide Family*,"J. Biol. Chem. 269 : 22817-22822, 1994.
Bayer S., "Neurogenesis in the Rat Neostriatum," Intl. J. Devel. Neurosci. 2 : 163-175, 1984.

(Continued)

*Primary Examiner* — Chang-Yu Wang
(74) *Attorney, Agent, or Firm* — Ropes & Gray LLP; James F. Haley, Jr.; Yang Xu

(57) ABSTRACT

The invention provides methods of treating a subject having a disease, disorder or condition of the central nervous system. The methods include administering TGF-α polypeptides, related polypeptides, fragments and mimetics thereof useful in stimulating progenitor cell or stem cell proliferation, migration and differentiation. The methods of the invention are useful to treat and prophylactically ameliorate neurological tissue injury in vivo.

16 Claims, 3 Drawing Sheets

OTHER PUBLICATIONS

Bayer, et al., "Directions in Neurogenetic Gradients and Patterns of Anatomical Connections in the Telencephalon," Prog. Neurobiol. 29 : 57-106, 1987.

Beerli, et al., "Epidermal Growth Factor-related Peptides activate Distinct Subsets of ErbB Receptors and Differ in Their Biological Activities," J. of Biol. Chem., 271(11):6071-6076, Mar. 15, 1996.

Blomquist, et al., "Vaccinia virus 19-kilodalton protein: Relationship to several mammalian proteins, including two growth factors," Proc. Natl. Acad. Sci. USA 81 : 7363-7367, 1984.

Book by William Broad and Nicholas Wade, "Betrayers of the Truth", Simon and Schuster, p. 54 (1982).

Boonstra, et al., 1995 Cell Biology Int'l 19(5):413-430.

Borgundvaag, et al., "Dopamine receptor activation inhibits estrogen-stimulated transforming growth factor-alpha gene expression and growth in anterior pituitary, but not in uterus," Endocrinol. 130 : 3453-3458, 1992.

Brazelton, T., "From Marrow to Brain: Expression of Neuronal Phenotypes in Adult Mice," (2000) Science 290:1775.

Burgess, et al., "Possible Dissociation of Heparin-binding and Mitogenic Activities of Heparin-binding (Acidic Fibroblast) Growth Factor-1 from Its Receptor-binding Activities by Site-directed Mutagenesis of a Single Lysine Residue", J of Cell Bio. 1990, 111:2129-2138.

Carpenter, et al., "antibodies to the epidermal growth factor receptor block the biological activities of sarcoma growth factor", PNAS 80(18):5627-30, 1983.

Casper, et al., "EGF Enhances the Survival of Dopamine Neurons in Rat Embryonic Mesencephalon Primary Cell Culture," J. Neurosci, Res. 30:372-381, 1991.

Casper, et al., "Epidermal Growth Factor and Basic Fibroblast Growth Factor Protect Dopaminergic Neurons from Glutamate Toxicity in Culture," J. Neurochem. 65:1016-1026, 1995.

Catapano, et al., "Human Fetal Precursor Cells are Capable of Survival, Neuronal Differentiation, and Integration Following Transplantation into Neonatal Rat Brain," Soc. Neurosci. Abstr. 23 : 345, 1997.

Centers for Disease Control and Prevention, www.cdc.gov.

Chalazonitis A. et al., Transforming Growth Factor , But Not Epidermal Growth Factor, Promotes the Survival of Sensory Neurons In Vitro In Vitro 1992 Journal of Neuroscience 12(2):583-594.

Clarke, et al., "Reactive astrocytes express the embryonic intermediate neurofilament nestin," Neuroreport, 5 : 1885-1888, 1994.

Code, et al., "Some transforming growth factor-alpha connections and their colocalization with enkephalin in the rat central nervous system," Brain Res. 421:401-405, 1987.

Coffey, et al., "Production and auto-induction of transforming growth factor-α in human keratinocytes," Nature 328: 817-820, 1987.

Connor B., et al., "The Role of Neuronal Growth Factors in Neurodegenerative Disorders of the Hyman Brain," 1998 Brain Research Reviews 27: 1-39.

Cooper, et al, "Intrastriatal transforming growth factor α delivery to a model of parkinson's disease induces proliferation and migration of endogenous adult neural progenitor cells without differentiation into dopaminergic neurons", J. Neurosci. Oct. 13, 2004; 24(41):8924-8931.

1995 issue of SIGMA catalogue, Biochemicals Organic Compounds (Diagnostic Reagents) cover, copyright page and p. 1274.

Craig, et al., "In Vivo Growth Factor Expansion of Endogenous Subependymal Neural Precursor Cell Populations in the Adult Mouse Brain", Journal of Neuroscience, New York, NY vol. 16, No. 8, Apr. 15, 1996, pp. 2649-2658, XP001002077, ISSN: 0270-6474.

Defeo-Jones, et al., "Structure-Function Analysis of Synthetic and Recombinant Derivatives of Transforming Growth Factor Alpha", Molecular & Cellular Biology (1988); 8(8):2999-3007.

Derynck, "Transforming Growth Factor-α" (1990) Molecular Reproduction and Development 27:3-9.

Dunbar, et al., "Structure-function and biological role of betacellulin," Intn'l J. of Biochem. & Cell Biol., 32(8):805-815, 2000.

Dhuria SV—J Pharm Sci 99:1654-1673—Intranasal delivery to the central nervous system: mechanisms and experimental considerations.—(2010).

Earp, et al., "Epidermal Growth Factor (EGF) Stimulates EGF Receptor Synthesis," J. Biol. Chem. 261 : 4777-4780, 1986.

Ebadi, et al, "Neurotrophins and Their Receptors in Nerve Injury and Repair" (1997) Neurochem. Int. 30(4/5):347-374.

Eriksson, et al., "Neurogenesis in the adult human hippocampus," NatMed 4:1313-1317—(1998).

Ezeonu, et al., "Cell fate decisions in a human retinal precursor cell line: basic fibroblast growth factor- and transforming growth factor-alpha-mediated differentiation", DNA Cell Bio.Sep. 2000; 19(9):527-37.

Ezeonu, et al., "Density-dependent differentiation in nontransformed human retinal progenitor cells in response to basic fibroblast growth factor-and transforming growth factor-alpha", DNA Cell Biol, Oct. 2003; 22(10): 607-20.

Faber-Elman et al, "Involvement of Wound-associated Factors in Rat Brain Astrocyte Migratory Response to Axonal Injury: In Vitro Simulation" (1996) J. Clin. Invest. 97(1):162-171.

Fallon, et al., "In vivo Induction of Massive Proliferation, directed Migration, and Differentiation of Neural Cells in the Adult Mammalian Brain", Proceedings of the National Academy of Sciences, USA, vol. 97:14686-14691 (2000).

Fallon, et al., "Functional Implications of the Anatomical Localization of Neurotrophic Factors", Neutrophic Factors, (Loughlin, S. E. & Fallon, J. H., Eds) 1993 Academic Press, New York, pp. 1-24.

Fallon, et al, "Localization of Cells Containing Transforming Growth Factor-α Precursor Immunoreactivity in the Basal Ganglia of the Adult Rat Brain", Growth Factors; 1990, 2:241-250.

Fallon, et al., "Epidermal Growth Factor Receptor mRNA Is Increased in the Striatum of Rats With 6ohba Lesions of the Substantia Kigra and Intrastriatal Transplants in the Caudate Putamen" Department of Anatomy and Neurobiology, University of California, Irvine, Irvine, CA 92717, Society for Neuroscience Abstracts vol. 20, 1994, p. 40.

Fallon, et al., "The Rat Nervous System", G. Paxinos, Ed., pp. 215-237, Academic Press, San Diego, 1995.

Fallon, et al., Cerebral Cortex, E.G. Jones and A. Peters, Eds., vol. 6, pp. 41-127, Plenum Press, New York, 1987.

Fallon, et al., "Epidermal Growth Factor Immunoreactive Material in the Central Nervous System: Location and Development," Science 224:1107-1109.

Fallon, "Growth Factors in the Basal Ganglia", The British Library—"The world's knowledge", (1986) pp. 247-260.

Fallon—Growth Factors 6:139-157—Localization of Acidic Fibroblast Growth Factor Within the Mouse Brain Using Biochemical and Immunocytochemical Techniques—(1992).

Fernaud-Espinoza, et al., "Differential Activation of Microglia and Astrocytes in Aniso- and Isomorphic Gliotic Tissue," Glia 8 : 277-291, 1993.

Ferrari, et al., "Epidermal Growth Factor Exerts Neuronotrophic Effects on Dopaminergic and GABAergic CNS Neurons: Comparison With Basic Fibroblast Growth Factor," J. Neurosci, Res. 30:493-497, 1991.

Ferri, et al., "Regulation of regional differences in the differentiation of cerebral cortical neurons by EGF family-matrix interactions," Development 121 : 1151-1160, 1995.

Fishman Renata et al, "Multiple Receptor Systems Promote CNS Neural Migration" Database Biosis Online, Biosciences Information Service, Philadelphia, PA, US; 1993, Database Accession No. PREV199396090915 XP002240919 & Journal of Neuroscience vol. 13, No. 8, 1993, pp. 3485-3495.

Freed, et al., "Eight Years Experience with Fetal Neurotransplantation in Patients with Advanced Parkinsons Disease," Soc. Neurosci. Abstr. 22 : 481-3, 1996.

Frey, II et al., "Delivery of 125I-NGF to the Brain via the Olfactory Route," Drug Delivery 4:87-92, 1997.

Friguls, et al., "Activation of ERK and Akt signaling in focal cerebral ischemia: modulation by TGF-α and involvement of NMDA Receptor", Neurobiology of Disease 11, 443-456 (2002).

Fuxe, et al., "Trophic Regulation of the Basal Ganglia: Focus on Dopamine Neurons", Journal Of Chemical Neuroanatomy 9 (1995) 79-80, Elsevier Science Ltd., Oxford UK, 1994, 618 pp., ISBN 0-08-042276-4.

Ghashghaei, et al., "Neuronal migration in the adult brain: are we there yet?", Nature Reviews Neuroscience, 8:141-151 (2007).

Gill, "Regulation of EGF Receptor Expression and Function" (1990) Molecular Reproduction and Development 27:46-53.
Gleason, et al., "Ependymal stem cells divide asymmetrically and transfer progeny into the subventricular zone when activated by injury", Neuroscience, vol. 156, Issue 1, Sep. 22, 2008, pp. 81-88.
Gomez-Pinilla, et al., "Epidermal growth factor receptor immunoreactivity in rat brain. Development and cellular locations," Brain Res. 438:385-390, 1988.
Gould E., et al., "Neurogenesis in the Neocortex of Adult Primates," (Science 286:548-552—1999) p. 3, 13.
Greengard, et al., "Beyond the dopamine receptor: the DARPP-32/protein phosphatase-1 cascade," Neuron 23:435-447—(1999).
Grotendorst, et al., "EGF and TGF-alpha Are Potent Chemoattractants for Endothelial Cells and EGF-like Peptides are Present at Sites of Tissue Regeneration," J. Cell. Physiol. 1989. 139:617-623.
Guerra-Crespo, et al., "Intranasal administration of PEGylated transforming growth factor-alpha improves behavioral deficits in a chronic stroke model." J. Stroke Cerebrovasc Dis. Jan. 2010:19(1):3-9.
Guerra-Crespo, et al., "Transforming Growth Factor-Alpha Induces Neurogenesis and Behavioral Improvement in a Chronic Stroke Model." Neuroscience, 160, 470-483 (2009).
Hadjiconstantinou, et al., "Epidermal Growth Factor Enhances Striatal Dopaminergic Parameters in the 1-Methyl-4-Phenyl-1,2,3,6-Tetrahydropyridine-Treated Mouse," J. Neurochem. 57:479-482, 1991.
Hefti F., "Neurotrophic Factor Therapy for Nervous System Degenerative Diseases," J. Neurobiol. 25:1418-1435, 1994.
Heidenkummer, et al., "Immunohistochemical localization of epidermal growth factor receptor in a human epiretinal membrane," (1991) Graefe's Arch Clin Exp Ophthalmol 229:492-496.
Hishiki, et al., "Glial Cell Line-derived Neurotrophic Factor/Neurturin-induced Differentiation and Its Enhancement by Retinoic Acid in Primary Human Neuroblastomas Express c-Ret, GFRα-1, and GFRα-2," Cancer Res. 58 : 2158-2165.
Jackowski et al, "Neural injury repair: hope for the future as barriers to effective CNS regeneration become clearer", Br. J. of Neurosurg., 9:303-317, 1995.
Jin K., "Neurogenesis in dentate subgranular zone and rostral subventicular zone after focal cerebral ischemia in the rat," Proc Natl Acad Sci U S A 98:4710-4714—(2001).
Jonathan et al, "The Ortega Hypothesis", Science, vol. 178, pp. 368-375 (1972).
Ju, et al., "TGFα Enhances Locomotion of Cultured Human Keratinocytes," J. Invest. Dermatol. 100 : 628-632, 1993.
Junier, et al., "Transforming Growth Factor α (TGFα) Expression in Degenerating Motoneurons of the Murine Mutant Wobbler: A Neuronal Signal for Astrogliosis?," J. Neurosci. 14 : 4206-4216, 1994.
Junier M-P., "What role(s) for TGFα in the central nervous system?," Prog. Neurobiol. 2000. 62:443-473.
Kelly, et al., "Amphetamine and Apomorphine Responses in the Rat Following 6-OHDA Lesions of the Nucleus Accumbens Septi and Corpus Striatum," Brain Research, 94(3):507-522, Sep. 5, 1974.
Kesavan, et al., "Regulation of stability and synthesis of EGF-receptor MRNAs encoding for intact and truncated receptor forms," Oncogene 5 : 483-488, 1990.
Khalid Shah, "Neural Stem Cells and Armed Derivatives: Fate and Therapeutic Potential in the Brain", Gene Therapy and Regulation, 3(1):91-109, (2007).
Kireeva, et al., "Cyr61, a product of a growth factor-inducible immediate-early gene, promotes cell proliferation, migration, and adhesion," Mol. Cell. Biol., 16:1326, 1996.
Kirschenbaum, et al., "In vitro Neuronal Production and Differentiation by Precursor Cells Derived from the Adult Human Forebrain," Cerebral Cortex 4 : 576-589, 1994.
Knusel, et al., "Selective and Nonselective Stimulation of Central Cholinergic and Dopaminergic Development in vitro by Nerve Growth Factor, Basic Fibroblast Growth Factor, Epidermal Growth Factor, Insulin and the Insulin-like Growth Factors I and II," and nonJ. Neurosci. 10:558-570, 1990.
Kornblum, et al., "Prenatal Ontogeny of the Epidermal Growth Factor Receptor and Its Ligand, Transforming Growth Factor Alpha, in the Rat Brain," (1997) Jln. of Comparative Neurology 380:249-261.

Krushel, et al., "Neural cell adhesion molecule (N-CAM) inhibits astrocyte proliferation after injury to different regions of the adult rat brain," Proc. Natl. Acad. Sci . USA 92 : 4323-4327, 1995.
Kudlow, et al, "Inability of Anti-epidermal Growth Factor Receptor Monoclonal Antibody to Block "Autocrine" Growth Stimulation in Transforming Growth Factor-secreting Melanoma Cells", J. Biol Chem 259(19):11895-900, 1984.
Kudlow, et al., "Transforming Growth Factor-a in the Mammalian Brain," J. Biol. Chem. 264:3880-3883, 1989.
Kuhn, et al., "Epidermal Growth Factor and Fibroblast Growth Factor-2 Have Different Effects On Neural Progenitors in the Adult Rat Brain." The Journal of Neuroscience, 17(15):5820-5829, Aug. 1, 1997.
Lachyankar, et al., "CNS Precursor Cells That Express TRK Receptors: Induction of Different Cell Fates by Neurothrophins," Soc. Neurosci. Abstr. 22 : 394.7, 1996.
Lazar, et al., "Regional Distribution and Developmental Expression of Epidermal Growth Factor and Transforming Growth Factor-α mRNA in Mouse Brain by a Quantitative Nuclease Protection Assay," J. Neurosci. 12:1688-1697, 1992.
Lee et al., "Developmental expression of rat transforming growth factor-alpha mRNA", Mol. Cell. Biol. 5:3655-3646, 1985.
Lee, et al., "Transforming growth factor alpha: expression, regulation, and biological activities," Pharmacol Rev 47:51-85—(1995).
Lefebvre, et al., "Regeneration of the neurosensory structures in the mammalian inner ear" (1997) Acta oto rhino-laryngologica belg. 51:1-10.
Leker, et al., "Transforming growth factor α induces angiogenesis and neurogenesis following stroke", Neuroscience 163 (2009) 233-243.
Lendahl, et al., "CNS Stem Cells Express a New Class of Intermediate Filament Protein," Cell 60 : 585-595, 1990.
Levine, et al., "Sonic Hedgehog Promotes Rod Photoreceptor Differentiation in Mammalian Retinal Cells In Vitro," J. Neurosci. : 6277-6288, 1997.
Lin, et al., "Expression of CD34 in endothelial cells, hematopoietic progenitors and nervous cells in fetal and adult mouse tissues," Eur. J. Immunol. 1995. 25:1508-1516.
Lindvall, et al., "Stem cells for the treatment of neurological disorders," Nature 441:1094-1096—(2006) p. 14.
Linnemann, et al.,"Expression of NCAM mRNA and Polypeptides in Aging Rat Brain," Int. J. Devel. Neurosci. 11 : 71-81, 1993.
Literature Search of Science Citations Index (Scisearch) database of Knight-Ridder Information Service, formerly the Dialog® Information Retrieval Service with complete list of citations and abstracts for articles citing Fallon et al. PNAS 97:14686-14691 (2000).
Literature Search Results from Science Citation Index (SciSearch) database for articles citing Kohler and Milstein article, Nature 256:495 (1975).
Lois, et al., "Proliferating subventricular zone cells in the adult mammalian forebrain can differentiate into neurons and glia," Proc. Natl. Acad. Sci. USA 90:2074-2077, 1993.
Lois, et al., "Chain Migration of Neuronal Precursors," Science 271 : 978-981, 1996.
Lokeshwar, et al., "Protamine Enhances Epidermal Growth Factor (EGF)-stimulated Mitogenesis by Increasing Cell Surface EGF Receptor Number," J. Biol. Chem. 264:19318-19326, 1989.
Loughlin, et al., "Mesostriatal Projections from Ventral Tegmentum and Dorsal Raphe: Cells Project Ipsilaterally or Contralaterally But Not Bilaterally", Neurosci. Lett. 32 : 11-16, 1982.
Loughlin et al., "6-OHDA lesion and TGF a infusion-induced plasticity in the nigrostriatal dopamine system—Tracing changes with markers for neurodegeneration", (1995) Soc. Neursci. Abs.
Loughlin, et al., "Efficacy of Intrastriatal Transplants: Role of Trophic Factors", The Basal Ganglia IV, (Percheron, G., et al., Eds) 1994, Plenum Press, New York, pp. 205-212.
Loughlin, et al., "Transforming Growth Factor Alpha: A Potential Role in the Efficacy of Intrastriatal Transplants", (1992) Soc. Neurosci. Abs.
Loughlin, et al.,"Striatal Transforming Growth Factor Alpha: Plasticity of Expression and Effects of Infusions of Dopaminergic Afferents", (1993) Soc. Neurosci. Abs.

Loughlin, et al., "Postnatal Ontogeny of Transforming Growth Factor, Alpha and Epidermal Growth Factor mRNA in Rat Brain", Dept. Anst. and Neurobio., Univ Calif., Irvine, Irvine, CA 92717, Society for Neuroscience Abstracts vol. 20, 1994, p. 40.

Louis, et al., "In vivo administration of EGF directly into the adult mouse subventricular zone has a greater effect on the frequency of neural progenitors than neural stem cells." Presented at Keystone 2005 by StemCell Technologies, Inc. www.stemcell.com.

Lundberg, et al., "Conditionally Immortalized Neural Progenitor Cells Grafted to the Striatum Exhibit Site-Specific Neuronal Differentiation and Establish Connections with the Host Globus Pallidus", Neurobiology of Disease, 3(1):33-50, Feb. 1996.

Luskin, M., "Restricted Proliferation and Migration of Postnatally Generated Neurons Derived from the Forebrain Subventricular Zone," Neuron 11 :173 -189, 1993.

Ma, et al., "Intranasal delivery of transforming growth factor-betal in mice after stroke reduces infarct volume and increases neurogenesis in the subventricular zone," BMC Neurosci 9:117—(2008).

Martinez-Morales et al., "Vitronectin is expressed in the ventral region of the neural tube and promotes the differentiation of motor neurons," Development 124 : 5139-5147.

McInnes, et al., "Growth Factor Receptors: Structure, Mechanism, and Drug Discovery" (1998) Protein Engineering Network of Centres of Excellence, Univ. of Alberta, Canada.

Mezey, et al., "Turning Blood into Brain: Cells Bearing Neuronal Antigens Generated in Vivo from Bone Marrow," (2000) Science 290:1779.

Mogi, et al., "Interleukin-1B, interleukin-6, epidermal growth factor and transforming growth factor-α are elevated in the brain from parkinsonian patients," Neurosci. Lett. 180 : 147-150, 1994.

Morrison, et al., "Trophic Stimulation of Cultured Neurons from Neonatal Rat Brain by Epidermal Growth Factor," Science 238:72-75, 1987.

Morshead, et al., "Postmitotic Death Is the Fate of Constitutively Proliferating Cells in the Subependymal Layer of the Adult Mouse Brain," J. Neurosci. 249-256, 1992.

Morshead, et al., "Neural Stem Cells in the Adult Mammalian Forebrain: A Relatively Quiescent Subpopulation of Subependymal Cells," Neuron 13 : 1071-1082, 1994.

Nakatomi, et al., "Regeneration of Hippocampal Pyramidal Neurons after Ischemic Brain zInjury by Recruitment of Endogeneous Neural Progenitors," Cell, 110:429-441 Aug. 23, 2002.

"New stroke therapy successful in rats: protein completely restores motor function", http://www.sciencedaily.com/releases/2010/01/100112135034.htm, Jan. 12, 2010.

NeuroRepair Validates IP with Lab's Success in New Stroke Therapy, httn://www.nrweb.com/releases/neuroregenerative/theranv/nrweb3583304.htm.

Nieto-Sampedro, et al., "Epidermal growth factor receptor immunoreactivity in rat brain astrocytes. Response to injury," Neurosci. Lett. 91 : 276-282, 1988.

Nihei, et al., "Newoflament and Neural Cell Adhesion Molecul.e Immunocytochemistry of Huntington's Disease Striatum," Ann. Neurol. 31 : 59-63, 1992.

Otto, et al., "Basic FGF Reverses Chemical and Morphological Deficits in the Nigrostriatal System of MPTP-Treated Mice," J. Neuroscience, 10:1912-1921 (1990).

Pagani, et al., "Tissue-specific Splicing Pattern of Fibronectin Messenger RNA Precursor during Development and Aging in Rat," J. Cell Biol. 113 : 1223-1229, 1991.

Pan, et al., "TGFα and the Blood-Brain Barrier: Accumulation in Cerebral Vasculature", Exp. Neurol. 1999. 160:454-459.

Panagakos F., "Transforming Growth Factor—Alpha Stimulates Chemotaxis of Osteoblasts and Osteoblast-like Cells In Vitro," Biochem. Mol. Biol. Int. 33 : 643-650, 1994.

Pardridge WM, "Drug Targeting to the Brain," Pharm Res 24:1733:1744 (2007).

Park, et al., "Protection from 1-methyl-4-phenylpyridinium (MPP+) toxicity and stimulation of regrowth of MPP+-damaged dopaminergic fibers by treatment of mesencephalic cultures with EGF and basic FGF," Brain Res. 599:83-97, 1992.

Pawson et al. "Assembly of Cell Regulatory Systems Through Protein Interaction Domains", 2003, Science 300:445-452.

Pesheva, et al., "Expression and localization of the Fibronectin Receptor in the Mouse nervous System," J. Neurosci. Res. 20 : 420-430, 1988.

Pezzoli, et al., "Intraventricular Infusion of Epidermal Growth Factor Restores Dopaminergic Pathway in Hemiparkinsonian Rats", Movement Disorders (1991); 6(4):281-287.

Poltorak, et al., "Effects of Frontal Cortical Lesions on Mouse Striatum: Reorganization of Cell Recognition Molecule, Glial Fiber, and Synaptic Protein Expression in the Dorsomedial Striatum," J. Neurosci. 13 : 2217-2229, 1993.

Popa-Wagner, et al., "Decortication and striatal mRNA: Increases of mRNA for fibronectin, but not of NCAM or α-1 tubulin," Neuroreport 3 : 853-856, 1992.

Prieto, et al., "Localization during Development of Alternatively Spliced forms of Cytotactin mRNA by In Situ Hybridization," J. Cell Biol. 111: 685-698, 1990.

Quirion, et al., "Visualization of Growth Factor Receptor Sites in Rat Forebrain," Synapse 2:212-218, 1988.

Rahman M—Neurosurg Focus 27:E12—Early history of the sterotactic apparatus in neurosurgery—(2009).

Rakic P "Limits of Neurogenesis in Primates", Science 227:1054-1056 (1985).

Ray et al., "Characterization of Neural Progenitor Cells Isolated and Cultured From Different Regions of Adult Rat Spinal Cord," Soc. Neurosci. Abstr. 22 : 394-5 1996.

Raymond et al., "Characterization of Epidermal Growth Factor Receptor Induction by Retinoic Acid in a Chemically Transformed Rat Liver Cell Line", Cell. Growth Diff. 1 : 393-399.

Reid et al, "Radial Migration of Subependymal Cells in the Adult Rodent Forebrain", (1996) Soc. Neurosci. Abs.

Reid et al, Tyrosine Hydroxylase Immunoreactive Cells in Adult Rat Striatum After Transforming Growth Factor Alpha Infusion & 6-Hydroxydopamine Lesion, Society for Neuroscience Abstracts vol. 20, 1994, p. 40.

Reid et al, Abstracts,Society of Neuroscience Abstracts, vol. 22 Part 3, 26th Annual Meeting, Washington, D.C. Nov. 16-21, 1996.

Reid et al, Review of "Trophic regulation of the basal ganglia" J. Chemical Neuroanatomy, 1995; 9(2):79-80.

Reid et al., Radial Migration of Subependymal Cells in the Adult Rodent Forebrain, Abstract, Aug. 7, 1997, Dept. of Anatomy and Neurobiology, Uni. of CA, Irvine, CA.

Reid. Dissertation 1997.

Reneker et al., "TGFa can act as a chemoattractant to perioptic mesenchymal cells in developing mouse eyes," Development 121 : 1669-1680, 1995.

Report prepared by National Institutes of Health "Stem Cells: Scientific Progress and Future Research Directions", Chapter 8, Jun. 2001.

Reynolds, "Generation of Neurons and Astrocytes from Isolated Cells of the Adult Mammalian Central Nervous System," (1992) Science 255:1707-1710, 1992.

Reynolds et al., "A Multipotent EGF-Responsive Striatal Embryonic Progenitor Cell Produces Neurons and Astrocytes," J. Neurosci. 12 : 4565-4574.

Rimaniol, A.C. et al., "Cerebral trauma induces a biphasic cortical production of TGFβ flanking the transient elevation of TNFα and IL6" (1994) Abstract, *J. NeuroImmunol.* 54:1-2.

Robert Miller. "The promise of stem cells for neural repair" Brain Research 1091:258-264(2006).

Rousselot, et al., "Embryonic (PSA) N-CAM reveals chains of migrationg neuroblasts between the lateral ventricle and the olfactory bulb of adult mice", The Journal of Comparative Neurology, 351(1):51-61, 1995.

Sagar et al, "Epidermal Growth Factor and Transforming Growth Factor α Induce c-fos Gene Expression in Retinal Muller Cells In Vivo" (1991) Jln. of Neuroscience Res. 29:549-559.

Sakane T, Pardridge WM, "Carboxyl-directed pegylation of brain-derived neurotrophic factor markedly reduces systemic clearance with minimal loss of biologic activity," Pharm Res 14:1085-1091 (1997).

Sanchez Ramos, "Adult Bone Marrow Stromal Cells Differentiate into Neural Cells in Vitro," (2000) Experimental Neurology 164:247.

Schmacher et al., "Intracerebral Implantation of Nerve Growth F Actor-Producing Fibroblasts Protects Striatum Against Neurotoxic Levels of Excitatory Amino Acids," Neuroscience, abstract only, 45:561-570 (1991).

Schneider et al., "Enhanced restoration of striatal dopamine concentrations by combined OM! ganglioside and neurotrophic factor treatments," Brain Res. 674:260-264, 1995.

Seroogy et al., "Proliferative zones of postnatal rat brain express epidermal growth factor receptor mRNA," Brain Res. 670:157-164, 1995.

Seroogy et al., "Cellular Localization of Transforming Growth Factor-α mRNA in Rat Forebrain", J. Neurochem. 60 : 1777-1782, 1993.

Seroogy et al., "Expression of EGF receptor mRNA in rat nigrostriatal system", Neuroreport 6:105-108, 1994.

Skolnick et al, "From genes to protein structure and function: novel applications of computational approaches in the genomic era", Trends in Biotech, 18(1):34-39, 2000.

Snyder et al., "Neuronal Regeneration, Reorganization, and Repair," (1997) Adv. Neurol. 72:121-132.

Snyder et al., "Multipotent neural precursors can differentiate toward replacement of neurons undergoing targeted apoptotic degeneration in adult mouse neocortex," (1997) *Proc. Natl. Acad. Sci. USA* 94:11663-11668.

Svendsen et al., "Survival and Differentiation of Rat and Human Epidermal Growth Factor-Responsive Precursor Cells Following Grafting into the Lesioned Adult Central Nervous System", 1996, Experimental Neurology 137: 376-388.

Szele et al., "Cortical Lesions Induce an Increase in Cell Number and PSA-NCAM Expression in the Subventricular Zone of Adult Rats," J. Compo Neurol. 368: 439-454, 1996.

Szele et al., "Pattern of Expression of Highly PolYsialYla Ted Neural Cell Adhesion Molecule in the Developing and Adult Rat Stria Tum," Neurosci. 60 : 133-144, 1994.

T Hart et al. "The use of animal models to investigate the pathogenesis of neuroinflammatory disorders of the central nervous system", Curr. Opin. Neurol. 2003. 16:375-383.

Tanabe et al., "Induction of motor neurons by Sonic hedgehog is independent of floor plate differentiation Yasuto Tanabe, Henk Roelink and Thomas M. Jessell," Curr. Biol. 5 : 651-658, 1995.

The recitation of "parenteral" in the 27th edition of Dorland's Illustrated Medical Dictionary (1988) p. 1231.

Thompson et al., "Regulation of Epidermal Growth Factor Receptor Gene Expression by Retinoic Acid and Epidermal Growth Factor," J. Biol. Chem. 264 : 3230-3234, 1989.

Toma et al., "Spatiotemporal Increases in Epidermal Growth Factor Receptors following Peripheral Nerve Injury," J. Neurosci. 12 : 2504-2515, 1992.

Twardzik et al., "Vaccinia virus-infected cells release a novel polypeptide functionally related to transforming [transferring] and epidermal growth factors", Aug. 1985, Proc. Natl. Acad. Sci 82:5300-5304.

Venero et al., "Intrastriatal Infusion of Nerve Growth Factor After Quinolinic Acid Prevents Reduction of Cellular Expression of Choline Acetyl Transferase Messenger Rna and Trka Messenger Rna, but not Glutamate Decarboxylase Messenger Rna," Neuroscience, abstract only, 61:257-268 (1994).

Ventrella et al, "Effect of intracerebroventricular infusion of epidermal growth factor in rats hemitransected in the nigro-striatal pathway", J. Neurosurg. (1993); 37:1-8.

Vicario-Abejon et al., "Cerebellar Precursors Transplanted to the Neonatal Dentate Gyrus Express Features Characteristic of Hippocampal Neurons," Neuron 15 : 105-114, 1995.

Vicario-Abejon et al., "Autoradiographic study of [IZI I]epidermal growth factor-binding sites in the mesencephalon of control and parkinsonian brains post-mortem," J. Neurosci. 15 : 6351-6363, 1995.

Villares et al., "Autoradiographic study of [125 I]epidermal growth factor-binding sites In the mesencephalon of control and parkinsonian brains post-mortem," Brain Res. 628: 72 -76, 1993.

Weickert et al, Striatal TGF-α: postnatal developmental expression and evidence for a role in the proliferation of subependymal cells (1995) Developmental Brain Research 86:203-216.

Weiss et al, "Multipoint CNS Stem Cells are Present in the Adult Mammalian Spinal Cord and Ventricular Neuroaxis", J. Neuroscience (1996); 16(23):7599-7609.

Werner et al., "Localization of Immunoreactive Epidermal Growth Factor Receptors in Human Nervous System," J. Histochem, Cytochem. 36:81-86, 1988.

Woodbury, "Adult Rat and Human Bone Marrow Stromal Cells Differentiate Into Neurons," (2000) J. Neuroscience Research 61:364.

Wyss-Coray et al., "Increased Central Nervous System Production of Extracellular Matrix Components and Development of Hydrocephalus in Transgenic Mice Overexpressing Transforming Growth Factor-J31," Am. J. Pathol. 147 : 53-67, 1995.

Xian et al., "Roles of Transforming Growth Factor-a and Related Molecules in the Nervous System," Mo. Neurobiol. 1999. 20:157-183.

Young et al., Neuronal Differentiation and Morphological Integration of Hippocampal Progenitor Cells Transplanted to the Retina of Immature and Mature Dystrophic Rats, (Mol. Cell. Neurosciences 16:197, 2000.

Zhang et al., "Transforming growth factor α and a PC12-derived growth factor induce neurites in PC12 cells and enhance the survival of embryonic brain neurons", Cell. Regul. 1:511-521, 1990.

Zhao C—Cell 132:645-660—Mechanisms and functional implications of adult neurogenesis—(2008).

Zurn e t al., "Combined Effects of GDNF, BDNF, and CNTF on Motoneuron Differentiation In Vitro," J. Neurosci. Res. 44 : 133-141, 1996.

*Neurorepair, Inc.* v. *The Nath Law Group*—Expert Report of Richard Warburg, Apr. 8, 2010.

*Neurorepair, Inc.* v. *The Nath Law Group*—Expert Report of James Fallon, Apr. 8, 2010.

*Neurorepair, Inc.* v. *The Nath Law Group*—Expert Report of Marc J. Tetel, Apr. 8, 2010.

*Neurorepair, Inc.* v. *The Nath Law Group*—Rebuttal Expert Report of James Fallon, Apr. 22, 2010.

*Neurorepair, Inc.* v. *The Nath Law Group*—Supplemental Expert Report of Marc J. Tetel, Oct. 25, 2010.

*Neurorepair, Inc.* v. *The Nath Law Group*—Rebuttal Expert Report of Richard Warburg, Apr. 23, 2010.

*Neurorepair, Inc.* v. *The Nath Law Group*—Supplemental to Rebuttal Expert Report of Richard Warburg, Oct. 13, 2010.

*Neurorepair, Inc.* v. *The Nath Law Group*—Second Rebuttal Expert Report of Richard Warburg, Nov. 12, 2010.

*Neurorepair, Inc.* v. *The Nath Law Group*—Second Supplemental to Rebuttal Expert Report of Richard Warburg, Mar. 24, 2011.

* cited by examiner

FIG. 1i
SUBCUTANEOUS TGFA-SIMULTANEOUS INFUSIONS
Rotations/30min

EXPERIMENTAL GROUP

| Animal no/w | 1 | 2 | 3 | 4 | 5 | 6 | 7 | 8 | 9 | 10 | 11 |
|---|---|---|---|---|---|---|---|---|---|---|---|
| 259 | 222 | 180 | 246 | 190 | 192 | 255 | 309 | 210 | 234 | 159 | 138 |
| 260 | 104 | 330 | 252 | 318 | 360 | 495 | 468 | 588 | 540 | 714 | 438 |
| 261 | 240 | 474 | 432 | 348 | 360 | 604 | 414 | 375 | 324 | 225 | 204 |
| 262 | -60 | 174 | 186 | 234 | 342 | 486 | 594 | 750 | 780 | 684 | 531 |
| 263 | 132 | 396 | 378 | 588 | 570 | 660 | 501 | 597 | 669 | 720 | 711 |
| 264 | 222 | 582 | 636 | 510 | 696 | 732 | 696 | 912 | 912 | 483 | 780 |
| 265 | 354 | 561 | 546 | 412 | 582 | 492 | 612 | 540 | 444 | 390 | 480 |
| 267 | 108 | 264 | 288 | 276 | 438 | 582 | 612 | 609 | 660 | 730 | 555 |
| 268 | 48 | 0 | 204 | 189 | 180 | 66 | 156 | 240 | 216 | 70 | 36 |
| 269 | 84 | 144 | 144 | 174 | 216 | 267 | 270 | 246 | 294 | 175 | 216 |
| 314 | 393 | 168 | 255 | 282 | 261 | 276 | 210 | 385 | 300 | 144 | 338 |
| 315 | 216 | 425 | 300 | 420 | 468 | 414 | 420 | 426 | 405 | 530 | 552 |
| Mean | 171.9 | 308.2 | 322.3 | 328.4 | 388.8 | 444.1 | 438.5 | 489.8 | 481.5 | 418.7 | 414.9 |
| Std. Dev. | 128.2 | 182.5 | 149.2 | 132.3 | 166.7 | 195.4 | 174.1 | 215.8 | 229.0 | 256.6 | 231.2 |

FIG. 1ii
SUBCUTANEOUS TGFA-SIMULTANEOUS INFUSIONS
Rotations/30min

CONTROLS
6OHDA+PBS

| Animal no/w | 1 | 2 | 3 | 4 | 5 | 6 | 7 | 8 | 9 | 10 | 11 |
|---|---|---|---|---|---|---|---|---|---|---|---|
| 271 | 0 | 60 | 30 | 408 | 522 | 528 | 660 | 552 | 570 | 462 | 624 |
| 272 | 66 | 186 | 421 | 498 | 396 | 486 | 576 | 378 | 576 | 582 | 624 |
| 273 | 36 | 30 | 201 | 108 | 390 | 240 | 222 | 403 | 615 | 240 | 483 |
| 274 | 288 | 222 | 186 | 210 | 360 | 222 | 336 | 108 | 102 | 99 | 237 |
| 275 | 522 | 534 | 609 | 288 | 498 | 750 | 684 | 528 | 522 | 498 | 711 |
| 276 | 0 | 0 | 63 | 183 | 240 | 272 | 270 | 300 | 252 | 279 | 282 |
| 277 | 22 | 504 | 336 | 435 | 516 | 714 | 570 | 750 | 924 | 918 | 942 |
| 278 | 282 | 156 | 459 | 318 | 360 | 450 | 522 | 594 | 414 | 588 | 270 |
| 279 | 0 | 181 | 600 | 300 | 744 | 441 | 930 | 798 | 747 | 798 | 438 |
| 280 | 444 | 420 | 324 | 402 | 444 | 480 | 534 | 354 | 378 | 435 | 399 |
| 281 | 354 | 234 | 312 | 474 | 240 | 702 | 690 | 558 | 567 | 159 | 474 |
| Mean | 183.1 | 229.7 | 321.9 | 329.5 | 428.2 | 480.5 | 544.9 | 483.9 | 515.2 | 459.8 | 498.5 |
| Std. Dev. | 198.7 | 183.1 | 193.4 | 126.2 | 142.8 | 186.8 | 206.8 | 200.9 | 225.7 | 256.8 | 213.4 |

| | | | | | | | | | | | |
|---|---|---|---|---|---|---|---|---|---|---|---|
| | | 0.4379 | 0.1579 | 0.4981 | 0.4924 | 0.2740 | 0.3265 | 0.0996 | 0.4731 | 0.3631 | 0.3524 | 0.1886 |

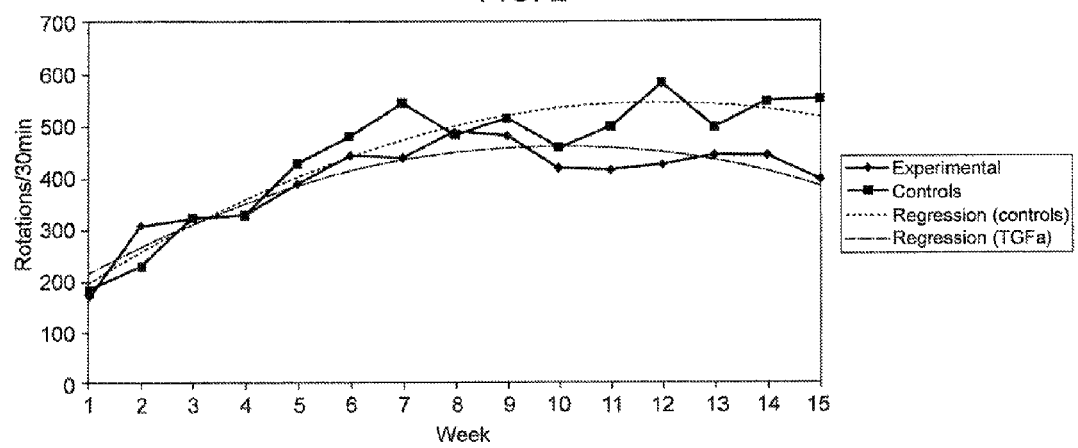

METHODS FOR TREATING A NEUROLOGICAL DISORDER BY PERIPHERAL ADMINISTRATION OF A TROPHIC FACTOR

CROSS-REFERENCE

This application is a continuation of U.S. patent application Ser. No. 10/167,384, filed Jun. 10, 2002 (now U.S. Pat. No. 7,795,202), which is a continuation-in-part of U.S. patent application Ser. No. 09/129,028, filed Aug. 4, 1998 (now U.S. Pat. No. 7,790,669), and claims the benefit of U.S. Provisional Patent Application 60/055,383, filed Aug. 4, 1997, U.S. Provisional Patent Application 60/328,725, filed Oct. 11, 2001, and U.S. Provisional Patent Application 60/297,518, filed Jun. 11, 2001, which applications are incorporated herein by reference in their entirety.

STATEMENT AS TO FEDERALLY SPONSORED RESEARCH

This invention was made in part with U.S. Federal Government support under National Institutes of Health grant nos. NS 0735-5; NS 26761; NS 10175. The U.S. Federal Government may have certain rights in this invention.

TECHNICAL FIELD

This invention is in the field of disorders of the central and peripheral nervous systems.

BACKGROUND

Neurogenesis in mammals is complete early in the postnatal period. Cells of the adult mammalian central nervous system (CNS) have little or no ability to undergo mitosis and generate new neurons. Thus, the generation of new CNS neurons in adult primates does not normally occur. This inability to produce new nerve cells in most mammals (and especially primates) may he advantageous for long-term memory retention; however, it is a distinct disadvantage when the need to replace lost neuronal cells arises due to injury or disease.

CNS disorders encompass numerous afflictions such as neurodegenerative diseases (e.g. Alzheimer's and Parkinson's), acute brain injury (eg. stroke, head injury, cerebral palsy) and a large number of CNS dysfunctions (e.g. depression, epilepsy, and schizophrenia). Degeneration in a brain region known as the basal ganglia can lead to diseases with various cognitive and motor symptoms, depending on the exact location. Other forms of neurological impairment can occur as a result of neural degeneration, such as cerebral palsy, or as a result of CNS trauma, such as stroke and epilepsy. In the case of Alzheimer's disease, there is a profound cellular degeneration of the forebrain and cerebral cortex. In the case of Parkinson's disease, degeneration is seen in the substantia nigra par compacta. This area normally sends dopaminergic connections to the striatum that are important in regulating movement. Dopamine is a catecholamine neurotransmitter that is particularly important in the control of movement. The great majority of brain dopamine is found in the striatum, and contained in neurons originating from a brain stem nucleus, the substantia nigra. The death of these cells, with a consequent loss of dopamine, is responsible for the symptoms of Parkinson's disease. Other dopaminergic neurons of the brain stem innervate the limbic system and cortex and abnormalities of these systems have been implicated in schizophrenia. Therapy for Parkinson's disease has centered upon restoring dopaminergic activity to this circuit through the use of pharmaceutical compounds and/or neurotrophic factors.

Neurotrophic factors are polypeptides that variously support the survival, proliferation, differentiation, size, and function of nerve cells. Most trophic factors can be assigned to one or another established family based upon their structure or binding affinities. Growth factors from various families, including the epidermal growth factor (EGF) family, have been demonstrated to support growth and differentiation of dopaminergic neurons of the nigrostriatal system. EGF has been localized to areas of the developing adult forebrain and to areas of the midbrain such as the globus pallidus, ventral pallidum, entopeduncular nucleus, substantia nigra, and the Islands of Calleja. The EGF receptor was localized by immunocytochemistry to astrocytes and subpopulations of cortical and cerebellar neurons in rat brain and to neurons in human autopsy brain specimens.

Transforming growth factor-alpha (TGF-α) is a member of the EGF family that has been shown to bind the EGF receptor, stimulate the receptor's tyrosine kinase activity, and elicit similar mitogenic responses in a wide variety of cell types. TGF-α also supports the survival of mesencephalic dopamine neurons in dissociated cell culture and supports the survival of cultured central neurons.

Treatment of CNS disorders has focused not only on the administration of trophic factors, but also on the administration of stem cells to replace those neural cells lost by natural cell death, injury or disease. For example, multipotent neural stem cells that are capable of producing progeny that differentiate into neurons and glia exist in adult mammalian neural tissue. Moreover, recent studies indicate that neuronal tissue can be generated from cells derived from adult bone marrow. These studies demonstrate that transplanted adult bone marrow stem cells can differentiate into neuronal cells.

Despite recent advances in treating neurological deficits, treatments still require the direct application of a trophic factor or infusion of stem cells to a site of injury or damage in the CNS in a subject in need of such treatment. Given the paucity of successful treatments for neurological deficits in general, there remains a need for additional methods that do not rely on invasive intracranial procedures or exogenous stem cells to achieve a result.

LITERATURE

U.S. Pat. No. 5,980,885; WO 98/22127; Reid et al. Society of Neuroscience Abstracts, Vol. 22 Part 3, 26th Annual Meeting, Washington, D.C. Nov. 16-21 1996; Reynolds (1992) *Science* 255:1707; Brazelton (2000) *Science* 290:1775; Mezey (2000) *Science* 290:1779; Sanchez-Ramos (2000) *Experimental Neurology* 164:247; Woodbury (2000) *J. Neuroscience Research* 61:364; Alexi et al. (1997) *Neurosci.* 78:73-86; WO 99/06060; WO 01/12127; WO 00/65028; Snyder et al. (1997) *Proc. Natl. Acad. Sci. USA* 94:11663-11668; Snyder et al. (1997) *Adv. Neurol.* 72:121-132; Fallon et al. (2000) *Proc. Natl. Acad. Sci. USA* 97:14686-14691.

SUMMARY

The present invention provides methods of treating injuries or damage to the CNS that do not require the direct administration of a trophic factor to a site of injury or the introduction of stem cells into the subject being treated.

The invention provides methods for promoting neurogenesis or modulating neural activity of injured, damaged or diseased central nervous system (CNS) tissue through the peripheral administration of a trophic factor. The methods comprise administration of a trophic factor that binds to an epidermal growth factor (EGF)/ErbB family receptor (i.e., an ErbB family receptor ligand) to any site peripheral to the central nervous system in a subject.

The invention provides methods comprising administration of TGF-α polypeptide, a TGF-α related polypeptide, a TGF-α functional fragment, or a TGF-α mimetic to a subject to modulate or promote neurogenesis or neural activity. By providing various ways to generate new glial and neuronal cells from endogenous progenitor cells, the invention also provides methods for inducing regeneration of tissues and neurological function. The invention provides methods for attracting a progenitor cell, or progeny thereof, to a site of injury or damage in the central nervous system of a subject by peripherally administering a therapeutically effective amount of a TGF-α polypeptide, a TGF-α related polypeptide, a TGF-α functional fragment, or a TGF-α mimetic to the subject. Thus, the invention features methods for generating, or regenerating, or modulating, neuronal tissues and their functions in vivo and for ameliorating neurological deficits, including inherited disorders, traumas, infections, autoimmune diseases and the like.

In one aspect, the invention provides a method for modulating neurogenesis at a site of injury or damage in the central nervous system of a subject by peripherally administering a therapeutically-effective amount of a TGF-α polypeptide, a TGF-α related polypeptide, a TGF-α functional fragment, or a TGF-α mimetic to the subject. While the invention is not limited by any particular mechanism of action, the administration can induce the proliferation, migration, differentiation (including dedifferentiation or redifferentiation) of a cell, such as a progenitor cell, or progeny thereof, to the site of injury or damage in the central nervous system. In an alternative aspect, the administration induces the proliferation, migration, or differentiation (including dedifferentiation or redifferentiation) of a cell, such as a progenitor cell, or progeny thereof, at or near the site of injury or damage in the central nervous system. In alternative aspects, the progenitor cell, and/or its progeny, express polypeptides comprising a CD34+, a Sca-1+, or a CD 117+ (c-kit+) polypeptide. In alternative aspects, the methods induce differentiation, or de-differentiation, of a cell, and the resultant cell expresses polypeptides comprising a CD34+, a Sca-1+, or a CD 117+ (c-kit+) polypeptide.

In alternative aspects of the methods of the invention, the progenitor cell is a pre-hematopoietic stem cell, a hematopoietic stem cell, an endothelial cell and a perivascular cell. However, the progenitor cell can be any cell at any level of development or differentiation that differentiates, e.g., de-differentiates or re-differentiates, in response to the methods of the invention.

In alternative aspects of the methods of the invention, the central nervous system injury or damage is a neurodegenerative disease, a traumatic injury, a neurotoxic injury, an ischemia (e.g., from an ischemic event), a developmental disorder, a disorder affecting vision, an injury or disease of the spinal cord, a demyelinating disease, an autoimmune disease, an infection and an inflammatory disease. However, it is understood that any neurological disorder benefited by the peripheral administration of a trophic factor that induces an endogenous progenitor cell, or progeny thereof, to directly or indirectly result in the repopulation of damaged neuronal tissue in the central nervous system is encompassed by the present invention. In one aspect, the disorder affecting vision effects or is related to the retina. In alternative aspects, the neurodegenerative disease is Alzheimer's disease, Huntington's disease, amyotrophic lateral sclerosis (ALS) and Parkinson's disease. In one aspect, the injury or damage results from a neoplastic lesion. In one aspect, the injury or damage results from radiation or chemotherapeutic treatment of the central nervous system.

In alternative aspects of the methods of the invention, the peripheral administration comprises subcutaneous administration, intravenous administration, intradermal administration, intramuscular injection, topical administration and oral administration.

In one aspect, the method further comprises mechanically disrupting tissue in the CNS, thereby directing translocation of the progenitor cell, or progeny thereof.

In one aspect, the method further comprises neurochemically blocking the activity of cells in the central nervous system, thereby directing migration of the progenitor cell, or progeny thereof.

The invention further provides a method for modulating neurogenesis or neural activity at a site of injury or damage in the central nervous system in a subject by peripherally administering a therapeutically effective amount of a nucleic acid comprising a nucleotide sequence encoding a TGF-α a polypeptide, a TGF-α related polypeptide, a TGF-α functional fragment, or a TGF-α mimetic. In one aspect, the nucleic acid sequence is present in an expression vector, including, e.g., naked DNA, plasmids, recombinant viruses, and the like. In one aspect, the nucleic acid sequence is operably linked to an expression control sequence, including, e.g., promoters, enhancers and the like.

In one aspect, the expression induces the proliferation, migration, or differentiation of a progenitor cell, or progeny thereof, into, at, or near the site of injury or damage resulting in modulation of neurogenesis or neural activity in the subject. In one aspect, the method further comprises neurochemically blocking the activity of cells in the CNS, thereby directing migration of the progenitor cell, or progeny thereof.

The invention further provides a method for treating, regenerating or repairing a central nervous system tissue of a subject in vivo, by contacting the tissue with TGF-α polypeptide, a TGF-α related polypeptide, a TGF-α functional fragment, or a TGF-α mimetic prior to, contemporaneously with, or subsequent to a tissue injury or damage in an amount effective to induce the proliferation, migration, or differentiation of a progenitor cell at or near the site of injury, thereby treating, regenerating or repairing the tissue.

The invention further provides a method for attracting a progenitor cell (e.g., a hematopoietic progenitor cell, a progenitor cell in a vascular endothelium or perivascular tissue, or a progenitor cell from bone marrow or other organ), or a progeny thereof, to a site of injury or damage in the central nervous system comprising administering a TGF-α polypeptide, a TGF-α related polypeptide, a TGF-α functional fragment, or a TGF-α mimetic, in a pharmaceutically acceptable carrier, to a site not associated with the site of injury or damage, sufficient to attract the cell to the site.

In alternative aspects, the progenitor cell is a non-neuronal progenitor cell, a pre-hematopoietic stem cell, a hematopoietic stem cell, an endothelial cell or is derived from a vascular endothelium and a perivascular cell.

The invention further provides a method for ameliorating a neurological deficit in a subject (e.g., treating a subject having a neurological deficit), the method comprising contacting a progenitor cell of the subject in vivo with a TGF-α polypeptide, a TGF-α related polypeptide, a TGF-α functional fragment, or a TGF-α mimetic, wherein the contacting results in a signal transduction sufficient to mobilize the progenitor cell, or progeny thereof, to a region of the central nervous system of the patient, wherein the progenitor cell differentiates into a neuronal cell and functions in a manner sufficient to ameliorate (e.g., reduce) the neurological deficit. In one aspect, the progenitor cell expresses polypeptides comprising a CD34+, a Sca-1+, or a CD 117+ (c-kit+) polypeptide.

The invention further provides a method for expansion of a progenitor cell comprising contacting the cell in vivo with an amount of a TGF-α polypeptide, a TGF-α related polypeptide, a TGF-α functional fragment, or a TGF-α mimetic effective to promote progenitor cell proliferation in vivo.

The invention further provides a method of directing the differentiation of an endogenous progenitor cell in a subject, the method comprising contacting the progenitor cell with TGF-α polypeptide, a TGF-α related polypeptide, a TGF-α functional fragment, or a TGF-α mimetic, whereby the progenitor cell differentiates at or near the site of damage or injury to a neuronal tissue and wherein the cell acquires the phenotypic characteristics of the differentiated cells of the neuronal tissue.

The invention provides a method for prophylactically ameliorating an effect of an injury in the central nervous system or the peripheral nervous system of a subject comprising: peripherally administering an effective amount of a TGF-α polypeptide to the subject, thereby prophylactically ameliorating the effect of an injury in the central nervous system or the peripheral nervous system of the subject.

All publications, GenBank sequences, patents and patent applications cited herein are hereby expressly incorporated by reference for all purposes. All publications, patents and patent applications, GenBank sequences, mentioned herein are incorporated herein by reference in full for the purpose of describing and disclosing the cell lines, vectors, and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIGS. 1i and 1ii present a table providing data for rotational behavior of animals treated with TGFα, and of control animals not treated with TGFα.

FIG. 2 is a graph of data showing mean rotations for TGF-α-treated animals and controls, spanning a fifteen-week time period. The data are the behavioral data for 24 animals receiving subcutaneous TGF-α and controls followed for 15 weeks. The data indicate that animals receiving subcutaneous TGF-α show a 20% reduction in motor deficits (p=0.0364) when compared to controls at week 15 post-infusion.

DETAILED DESCRIPTION

The present invention provides methods for using a trophic factor to treat injured or damaged tissue of the central nervous system (CNS). The present invention provides methods for peripherally administering a trophic factor, such as TGF-α, into a subject such that an endogenous progenitor cell (i.e., primitive stem cell) is induced to proliferate, and/or migrate, and/or differentiate at or into a site of injury or damage in the CNS. The invention is also directed to protecting or prophylactically ameliorating the central nervous system (CNS) and peripheral nervous system (PNS) from the effects of an injury (e.g., traumatic or chemical insult) by peripheral administration of a trophic factor.

The present invention provides a method for treating neurological disorder in a subject having a neurological disorder resulting from CNS damage or injury. The methods generally involve peripherally administering a trophic factor such as a TGFα polypeptide to the subject, such that a progenitor cell or progeny thereof is contacted with the trophic factor, and the progenitor cell is induced to proliferate and/or migrate and/or differentiate at or near or into a site of preexisting CNS damage or lesion in the subject. The trophic factor is administered in a pharmaceutically acceptable carrier and in an amount effective to stimulate the proliferation and/or migration and/or differentiation of the progenitor cell or progeny thereof at or near or into the site of the CNS damage or lesion, thereby treating the neurological disorder.

In vivo neurogenesis in the forebrain of the adult rat is demonstrated in the present study using a combination of a 6-hydroxydopamine (6-OHDA) lesion of the substantia nigra dopaminergic neurons and an exemplary embodiment of the invention comprising the peripheral administration of transforming growth factor α (TGF-α) as discussed below. In behavioral experiments, there was a significant reduction of apomorphine-induced rotations in animals receiving the peripheral TGF-α administration. These results show that progenitor cells are capable of proliferation, migration, and neurodifferentiation in response to the peripheral administration of a trophic factor. Accordingly, the methods of the invention can be used in the amelioration and treatment of both acute neural trauma and neurodegenerative diseases.

While the invention is not limited by any particular mechanism of action, the present study indicates that peripherally administered TGF-α exerts its effects on the proliferation, migration, and/or differentiation of cerebral blood vessel endothelial cells, perivascular cells, circulating HSCs and/or SVZ progenitor cells via activity initiated within the vascular compartment. The aforementioned cells are generally found: 1) within the lumen of a cerebral vessel; 2) integral with the cerebral vessel wall; or 3) associated with the periphery of a cerebral vessel. For example, an endothelial cell of a cerebral vessel can serve as a progenitor cell that is capable of generating neural cells according to the method of the invention. An endothelial cell possesses: 1) EGF receptors that also serve as TGF-α receptors; 2) the ability to proliferate in response to TGF-α; and 3) the ability to express CD34 in response to the appropriate stimulation. These characteristics are desirable but not limited solely to endothelial cells.

Recent studies have demonstrated the ability of bone marrow-derived progenitor cells to differentiate in vitro into neurons and for transplanted HSCs to migrate into the CNS and differentiate into neurons in vivo in the early postnatal (Mezey et al., Science 290:1779, 2000) and adult murine CNS (Brazelton et al., Science 290:1775, 2000). The newly generated neurons reported in the present study aggregate around blood vessels in different areas of the brain. This observation is consistent with reports that neural precursors proliferate within a vascular neuroangiogenic niche for recruitment of progenitor cells that give rise to neural tissue.

The present study demonstrates that the consistently close spatial orientation of newly generated neurons around intracerebral vessels, and their expression of HSC surface antigens, is indicative of a cerebral blood vessel-associated origin of these cells. CD34, Sca-1+, or CD 117+ (c-kit+) are widely used as markers for primitive HSCs. For example, HSCs in the perinatal and early postnatal periods in mice express CD34, but the expression of CD34 is greatly attenuated between postnatal weeks 7 and 10, so that in the adult mouse only about 20% of HSCs are CD34$^+$ and 80% are CD34$^-$. In the adult murine hematopoietic system it has been demonstrated that CD34$^-$ HSCs begin to express CD34 when stimulated to differentiate, so that the expression of CD34 has been related to the activation state of CD34$^-$ HSCs. The expression of CD34 reported in the present study may represent a similar reactivation of CD34 expression in pre-existing neurons, in response to either TGF-α infusion or the denervation injury. The presence of CD34$^+$ neurons specifically in the denervated areas, and their absence in the non-lesioned brain areas of the experimental animals, indicates that the CD34$^+$ neurons are generated in response to the presence of both a lesion and TGF-α.

The invention provides methods for the expansion of non-terminally differentiated cells ("progenitor cells") by contacting a progenitor cell or a population of progenitor cells with a TGF-α polypeptide, a TGF-α related polypeptide, mimetic, or a fragment having TGF-α activity, and stimulating the progenitor cells to proliferate, migrate and/or differentiate in vivo. Contacting is typically achieved by contacting the cell directly, e.g., soluble form or recombinantly expressed by a cell or immobilized on a solid surface, or by introducing into the cell a recombinant nucleic acid expressing a TGF-α polypeptide, a TGF-α related polypeptide, mimetic, or a fragment having TGF-α activity.

As used herein, "endothelium" or "endothelial cells" constitute the layer of cells that line the cavities of the heart and of the blood and lymph vessels, and the serous cavities of the body, originating from the mesoderm. Endothelial cells lining a blood vessel are linked to each other laterally by occluding junctions which may either form continuous belts to create permeability barriers (zonulae occludentes) and hold the cells together or in some cases discontinuous, spot-like contacts (maculae occludentes), allowing some leakage between cells. Endotheliocytes are also linked to each other, and often to other extravascular cells, by gap (communicating) junctions facilitating cooperation between cells connected in this way. Endothelium has important metabolic functions and a variety of enzyme systems have been located within or at the surfaces of endothelial cells. For example, vascular endothelial cells are required in the process of angiogenesis. Angiogenesis occurs during tissue regeneration and is facilitated by the migration and proliferation of existing endothelium and by the differentiation of connective tissue progenitor cells, such as, for example, pluripotent mesenchymal stem cells.

As used herein, an "SVZ progenitor cell" is a multipotential stem cell originating in the subventricular zone (SVZ) of the brain. As used herein, a "perivascular," cell is a cell that is situated around a blood vessel. Perivascular cells are in close proximity to the structure of the blood vessel wall and as such are capable of receiving chemical signals initiated from the lumen of the blood vessel and transduced through the wall of the blood vessel. Thus, a peripherally administered trophic factor that normally does not cross the blood brain barrier (BBB), such as TGF-α, can still influence the generation of neural tissue by acting on cells positioned near a cerebral blood vessel such as an SVZ progenitor cell or perivascular cell. As used herein, a "peripherally" administered trophic factor is administered at a site not directly associated with the injury or damage to be treated in the CNS. The method of the invention does not require the direct contact of the trophic factor with the injured or damaged neuronal tissue. Thus, a peripherally administered trophic factor can modulate neurogenesis or neural activity at a site of injury or damage in the central nervous system of a subject without having to cross the blood brain barrier (BBB) through signal transduction.

As used herein, a "progenitor cell" includes any non-terminally differentiated cell such as, for example, a stem cell including an adult stem cell. A progenitor cell has specific biochemical properties, may or may not divide, and can be triggered to adopt a different differentiation state but not necessarily a fully differentiated state, by responding to specific developmental signals. Encompassed within the definition of "progenitor cell" is a cell that has de-differentiated into a less differentiated cell and now possesses pluripotential capabilities. The present study envisions that those cells associated with a cerebral blood vessel, including endothelial cells, perivascular cells, circulating HSCs and/or SVZ progenitor cells possess pluripotential capabilities. Such cells are capable of responding to microenvironmental signals generated by both TGF-α and signals elaborated by the denervated neurons, and/or their supporting cells (astrocytes, oligodendrocytes and microglia), in a manner suitable for the generation of neural tissue by the method of the invention.

The terms "progenitor cell" and "stem cell" are often used interchangeably herein. Stem cell or progenitor cells mat can be stimulated in vivo to proliferate, migrate and/or differentiate when contacted by a TGF-α polypeptide, a related polypeptide, mimetic, or functional fragment thereof having TGF-α activity, include adult stem cells and precursor cells. Such stem cells and precursor cells include, for example, cells of hematopoietic tissue, neuronal tissue, perivascular tissue and endothelial cells.

Hematopoietic stem cells (HSCs) are the formative pluripotential blast cells found inter alia in bone marrow and peripheral blood that are capable of differentiating into the specific types of hematopoietic or blood cells, such as erythrocytes, lymphocytes, macrophages, and megakaryocytes. After mobilization of HSCs from bone marrow by administration of certain factors, such as G-CSF and W-CSF and subsequent recovery from peripheral blood, HSCs have also come to be referred to as peripheral blood progenitor cells (PBPCs).

Mesenchymal stem cells (MSCs) are the formative pluripotential blast cells found inter alia in bone marrow, blood, dermis and periosteum that are capable of differentiating into more than one specific type of mesenchymal or connective tissue (e.g., adipose, osseous, stroma, cartilaginous, elastic, and fibrous connective tissues) depending upon various influences from bioactive factors, such as cytokines. The potential to differentiate into cells such as osteoblasts and chondrocytes is retained after isolation and expansion in culture; differentiation occurs when the cells are induced in vitro under specific conditions or placed in vivo at or near the site of damaged tissue.

In addition to hematopoietic stem cells, bone marrow contains stem-like precursors for non-hematopoietic cells, such as osteoblasts, chondrocytes, adipocytes and myoblasts (Owen et al., 1988, in Cell and Molecular Biology of Vertebrate Hard Tissues, Ciba Foundation Symposium 136, Chichester, UK, pp. 42-60; Caplan, 1991, *J. Orthop. Res.* 9:641-650; Prockop, 1997, *Science* 276:71-74). Non-hematopoietic precursors of the bone marrow have been variously referred to as colony-forming-unit-fibroblasts, mesenchymal stem cells, and marrow stromal cells (MSCs). As used herein, "stromal cells", "colony forming fibroblasts", "marrow stromal cells", "adherent cells" and "MSCs" are used interchangeably and are meant to refer to the small fraction of cells in bone marrow which can serve as stem cell-like like precursors of osteocytes, chondrocytes, and adipocytes.

As used herein, a "pluripotent cell" is a cell that may be induced to differentiate, in vivo or in vitro, into at least two different cell types. These cell types may themselves be pluripotent, and capable of differentiating in turn into further cell types, or they may be terminally differentiated, that is, incapable of differentiating beyond their actual state.

Pluripotent cells include totipotent cells, which are capable of differentiating along any chosen developmental pathway. For example, embryonal stem cells (Thomson et al., Science, 282:1145, 1998) are totipotent stem cells. Pluripotent cells also include other, tissue-specific stem cells, such as hematopoietic stem cells, mesenchymal stem cells, neuronal stem cells, neuroectodermal cells, ectodermal cells, and endodermal cells, for example, gut endodermal cells and mesodermal stem cells which have the ability to give muscle or skeletal components, dermal components, such as skin or hair, blood cells, etc. "Developmental pathway" refers to a common cell fate that can be traced from a particular precursor cell. Progenitor cells are more primitive, i.e., less fated to a particular developmental pathway than mesenchymal stem cells or hematopoietic stem cells.

A "partially committed" cell is a cell type that is no longer totipotent but remains pluripotent. For example, an SVZ stem cell is partially differentiated but still capable of further differentiating into various neuronal tissue types. Similarly, non-terminally differentiated endothelial cells can be stimulated to differentiate into neuronal tissue.

A pluripotent progenitor cell can be responsive to a cell proliferation-modulating agent. As used herein, a "cell proliferation-modulating agent" is any agent that can promote or inhibit cell growth or differentiation.

As used herein, the term "trophic factor" refers to compounds with trophic actions that promote and/or control proliferation, differentiation, migration, and survival (sometimes even the death) of their target cells, and/or protect them from injury. Such factors include cytokines, neurotrophins, epidermal growth factor, fibroblast growth factor, platelet-derived growth factor, insulin-like growth factors, ciliary neurotrophic factor and related molecules, glial-derived growth factor and related molecules, schwanoma-derived growth factor, glial growth factor, stiatal-derived neuronotrophic factor, platelet-derived growth factor, hepatocyte growth factor, scatter factor (HGF-SF), transforming growth factor-beta and related molecules, neurotransmitters, and hormones. Those of skill in the art will readily recognize additional trophic factors which can be employed in the present invention (see, e.g., Lenfant et al., Growth Factors of the Vascular and Nervous Systems: Functional Characterization and Biotechnology: International Symposium on Biotechnology of Grow (S. Karger Publishing, 1992).

The term "growth factor," as used herein, includes those molecules that function as growth simulators (mitogens) or as growth inhibitors (sometimes referred to as negative growth factors). Growth factors are also known to stimulate cell migration (e.g., mitogenic cytokines), function as chemotactic agents, inhibit cell migration or invasion of tumor cells, modulate differentiated functions of cells, be involved in apoptosis, and promote survival of cells. Such factors can be secreted as diffusible factors and can also exist in membrane-anchored forms. They can, therefore, act in an autocrine, paracrine, juxtacrine, or retrocrine manner. A cytokine is one type of growth factor. A "cytokine" is polypeptide that acts as a humoral regulator at nano-to-picomolar concentrations and which, either under normal or pathological conditions, can modulate the functional activities of individual cells and tissues. A cytokine can mediate interactions between cells directly and/or can regulate processes taking place in the extracellular environment. Cytokines comprise interleukins, lymphokines, monokines, interferons, colony-stimulating factors, and chemokines, in addition to a variety of other proteins.

Growth factors further include epidermal growth factors (EGFs), transforming growth factors (TGFs), platelet-derived growth factors (PDGFs), fibroblast growth factors (FGFs), hepatocyte growth factors (HGFs), hematopoietic growth factors (HeGFs), tumor necrosis factor (TNF-$\alpha$), platelet-derived endothelial cell growth factor (PD-ECGF), insulin-like growth factor (IGF), interleukin-8, growth hormone, angiopoietin, vascular endothelial growth factor (VEGF), acidic and basic fibroblast growth factors (FGFs), transforming growth factor $\alpha$ (TGF-$\alpha$ or TGF-$\alpha$), and CYR 61 (Babic et al., Proc. Natl. Acad. Sci. USA, 95:6355, 1998; Kireeva et al., Mol. Cell. Biol., 16:1326, 1996). Such factors further include insulin, IGF-I, IGF-II, nerve growth factor, NGF receptor, EGF, TGF-$\alpha$, EGF receptor, neu, TGF-$\beta$1, TGF-$\beta$2, TGF-$\beta$3, inhibin $\alpha$, inhibin $\beta$, Müllerian inhibitory substance, TNF-$\alpha$/$\beta$, TNF-receptor (type 1), TNF-receptor (type 2), PDGF A-chain, PDGF B-chain, PDGF receptor $\alpha$, PDGF receptor $\beta$, a-FGF, b-FGF, wnt-2, hst/ks3, hepatocyte growth factor, HGF receptor (c-met), IL-1$\alpha$/$\beta$, ($\alpha$-chains) IL-2, IL-3, IL-4, IL-5, IL-6, IL-7, IL-9, IL-11, IL-12A (p35), IL-12B (p40), Interleukin 1 (type 1), Interleukin-2$\alpha$, Interleukin-2$\beta$, Interleukin-4, Interleukin-5$\alpha$, Interleukin-6, Interleukin-7, M-CSF (also called CSF-1), M-CSF receptor (c-fms), GM-CSF, GM-CSF receptor $\alpha$, GM-CSF receptor $\beta$, G-CSF, G-CSF receptor, stem cell factor, SCF receptor (c-kit), Erythropoietin (epo), epo receptor, and Leukemia inhibitory factor. Each of these molecules has been shown to induce cell proliferation, cell growth or differentiation in vivo. Other similar molecules that display cell growth or differentiation modulating activity are the heparin binding growth factors (HBGFs).

The invention provides a method for peripherally administering a trophic factor, such as TGF-$\alpha$ polypeptide, a related polypeptide, mimetic, or functional fragment thereof having TGF-$\alpha$ activity, in order to promote the repair of CNS tissue. A "polypeptide" or protein refers to a polymer in which the monomers are amino acid residues that are joined together through amide bonds. When the amino acids are $\alpha$-amino acids, either the L-optical isomer or the D-optical isomer can be used, the L-isomers being typical. A TGF-$\alpha$ polypeptide, a related polypeptide, mimetic, or functional fragment thereof is intended to encompass an amino acid sequence, including modified sequences such as glycoproteins, which exhibit TGF-$\alpha$ activity. The molecules (e.g., polypeptides) of the invention encompass amino acid sequences of TGF-$\alpha$ as well as polypeptides that have structural and/or functional characteristics of TGF-$\alpha$. For example, a polypeptide or a TGF-$\alpha$ related polypeptide of the invention may include a polypeptide that shares a cysteine disulfide bond structure similar to TGF-$\alpha$ such as a related family of proteins including vaccinia growth factor, amphiregulin precursor, betacellulin precursor, heparin binding EGF-like growth factor, epiregulin (rodent only), HUS 19878, myxomavirus growth factor (MGF), Shope fibroma virus growth factor (SFGF), and schwannoma derived growth factor. In addition, a molecule (e.g., a polypeptide) of the invention will have one or more functional characteristics related to TGF-$\alpha$ including, for example, the ability to interact with an EGF family receptor member, or stimulate proliferation or migration of progenitor cells.

The polypeptides for use in the methods of the invention are intended to cover substantially purified naturally occurring proteins, as well as those that are recombinantly synthesized, semi-synthetically synthesized, or synthetically synthesized.

In some embodiments, the trophic factor is a TGFα polypeptide. As used herein, the term "TGFα polypeptide" includes any known TGFα polypeptide; a fragment of a TGF-α polypeptide; a variant of a known TGFα polypeptide; a fusion polypeptide comprising a TGFα polypeptide; and a TGFα mimetic. Variants include polypeptides having substantial amino acid sequence identity to a known TGFα polypeptide; polypeptides comprising one or more conservative amino acid changes compared to a known TGFα polypeptide; and the like. Examples of known TGFα polypeptides include a TGFα polypeptide having amino acids 17-66 of the amino acid sequence provided in GenBank Accession No. P01135; and a TGFα polypeptide having amino acids 16-65 of the amino acid sequence provided in GenBank Accession No. P01134. For use in the methods of the invention, a TGFα polypeptide is biologically active, e.g., it retains the ability to induce differentiation and/or migration and/or proliferation of progenitor cells into a site of injury or damage in the CNS. Whether a TGFα polypeptide induces differentiation and/or migration and/or proliferation of progenitor cells into a site of injury or damage in the CNS can be determined using the methods described herein, and the methods described in WO 99/06060.

In addition, a TGF-α or related polypeptide can occur in at least two different conformations wherein both conformations have the same or substantially the same amino acid sequence but have different three dimensional structures so long as the have a biological activity related to TGF-α. Methods of using polypeptide or protein fragments of TGF-α are also encompassed by the invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related.

In general, polypeptides useful in the method of the present invention include peptides, or full length protein, that contain substitutions, deletions, or insertions into the protein backbone, that would still have from about 50% to about 70%, from about 70% to about 80%, from about 80% to about 90%, from about 90% to about 95%, from about 95% to about 98%, or higher, amino acid sequence identity to the original protein over the corresponding portion. A yet greater degree of departure from identity is allowed if like-amino acids, i.e. conservative amino acid substitutions, do not count as a change in the sequence. A TGF-α polypeptide fragment retains a biological activity associated with TGF-α.

Sequence identity (homology) to TGF-a polypeptide can be used to determine if is polypeptide is a composition used in a method of the invention; it can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra). Such procedures and algorithms include, for example, a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra (D)-amino acids, glycosylation sites, cytosine for specific disulfide bridge formation. The modified peptides can be chemically synthesized, or the isolated gene can be site-directed mutagenized, or a synthetic gene can be synthesized and expressed in a subject such that a neurological deficit is treated.

Solid-phase chemical peptide synthesis methods can also be used to synthesize polypeptide or fragments of polypeptides can be used in the present methods. Such method of synthesis have been known in the art since the early 1960's (Merrifield, R. B., J. Am. Chem. Soc, 85, 2149-2154 (1963) (See also Stewart; J. M. and Young, J. D., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81, 3998 (1984) and provide for synthesizing peptides upon the tips of a multitude of "rods" or C6 pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod and pin tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 43 1 A automated peptide synthesizer.

TGFα stimulates differentiation and/or proliferation and/o migration of stem cells of neural origin to sites or lesions in a neurological deficit. For example, Parkinson's Disease is characterized by resting tremor, rigidity, inability to initiate movement (akinesia) and slowness of movement (bradykinesia). The motor deficits are associated with progressive degeneration of the dopaninergic innervation to the nucleus accumbens and degeneration of noradrenergic cells of the locus ceruleus and serotonergic neurons of the raphe. Up to 80% of nigral dopamine neurons can be lost before significant motor deficits are manifest. TGF-α, when infused into rat brains over a period of time (e.g., days or weeks), is useful for the treatment of neurodegenerative disorders. Intracerebroventricular (ICV) or intrastriatal infusions of TGF-α over a period of 18 days induced neuronal stem cell proliferation, but degenerating, damaged or otherwise abnormal cells are present to facilitate migration of the neuronal stem cells to a site of injury on a scale sufficient to impact recovery from an associated neurological deficit (see PCT publications WO 99/06060 and WO 01/12127, incorporated herein by reference in their entirety). Forebrain neural stem cells migrate and affect treatment and recovery from a neurological deficit disorder including, for example, Parkinson's Disease, Huntington's Disease, Alzheimer's Disease and the like.

The present studies provide evidence that TGF-α, administered by a peripheral route, promotes neurogenesis of the central nervous system (CNS) and ameliorates abnormal motor behavior in an animal model of Parkinson's disease. Analysis of the brains of TGF-α-infused animals reveal the presence of recently generated neurons in multiple areas of the forebrain and midbrain, a few of which show terminal differentiation into dopamine (DA) producing neurons. As previously noted, TGF-α is unable to cross the BBB and typically accumulates within the cerebral vasculature. 6-OHDA, used in the present study to induce DA cell death in the SN, has been reported to disrupt the BBB but this disruption is limited to the mesencephalic areas and cerebral cortex in the vicinity of the needle tract, and not more rostral areas. Thus, it appears unlikely that TGF-α gains access to the more rostral cerebral parenchyma through the midbrain disruption of the BBB caused by 6-OHDA. For example, in the present study TGF-α is delivered via an intravascular route from a peripheral source. Accordingly, all cerebral vessels are perfused uniformly thereby diminishing the likelihood of a unidirectional influence imposed by intracranial placement of infusion cannulae. It is thus unlikely that the clustering of newly generated cells around blood vessels only in the denervated areas represents a chemoattractive or tropic response to intravascular growth factor, as this would be expected to result in a more widespread distribution of such cells around all cerebral vessels.

In another aspect, a nucleic acid comprising a nucleotide sequence encoding TGF-α polypeptide, a TGF-α related polypeptide, a functional fragment thereof, or a mimetic thereof is administered to a subject such that a TGF-α polypeptide, a TGF-α related polypeptide, a functional fragment thereof, or a mimetic thereof is expressed in vivo. As used herein, a "nucleic acid" (used interchangeably with the term "polynucleotide") refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. Nucleic acids suitable for use in the methods of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term "polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions.

Nucleic acids can be created which encode a fusion protein (e.g., a TGF-α polypeptide and another polypeptide, such as a targeting, sequence) and can be operatively linked to expression control sequences. "Operatively-linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents;

such elements may be located in the 5' or 3' regions of the of a polynucleotide sequence. Both constitutive and inducible promoters are included in the invention (see e.g., Bitter et al., Methods in Enzymology 153:516-544, 1987). For example, when cloning in mammalian cell systems, promoters derived from the genome of mammalian cells (e.g., metallothionein promoter) or from mammalian viruses (e.g., the retrovirus, long terminal repeat; the adenovirus late promoter; the vaccinia virus 7.5K promoter) may be used. Promoters produced by recombinant DNA or synthetic techniques may also be used to provide for transcription of the nucleic acid sequences of the invention. Tissue-specific regulatory elements may be used, including, for example, regulatory elements from genes or viruses that are differentially expressed in different tissues. Examples of tissue-specific regulatory elements include, tissue-specific promoters, such as milk-specific (whey), pancreatic (insulin or elastase), actin promoter in smooth muscle cells or neuronal (myelin basic protein) promoters such as GFAP (specific for glial cells; see also U.S. Pat. No. 6,066, 7260). Tissue specific promoters include the 5' or 3' flanking sequences of the beta-globin, elastase, α-fetoprotein, α-A crystalline, an erythroid specific transcriptional element and insulin genes (Yee, et al., *Proc. Natl. Acad. Sci.*, 86:5873-5877, 1989; Swift, et al., *Cell* 38:639, 1984; Storb et al., *Nature* (Lond.) 310:238; Grosscheldl et al., *Cell* 41:885, 1985; Shani, *Nature* (Lond) 314:238, 1985; and Chada et al, Nature (Lond), 1985).

A recombinant expression vector includes a polynucleotide sequence encoding a TGF-α polypeptide, related polypeptides, fragments or mimetics thereof. The expression vector typically contains an origin of replication, a promoter, as well as specific genes that allow phenotypic selection of the transformed cells. Vectors suitable for use in the invention include, but are not limited to the pMSXND expression vector for expression in mammalian cells (Lee and Nathans, *J. Biol. Chem.* 263:3521, 1988).

Mammalian cell systems which utilize recombinant, viruses or viral elements to direct expression may be engineered. For example, when using adenovirus expression vectors, a polynucleotide encoding a TGF-α polypeptide, a TGF-α related polypeptide, mimetic, or a fragment having TGF-α activity may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a TGF-α polypeptide or fragment thereof in infected hosts.

Direct in vivo gene transfer has been attempted with formulations of DNA trapped in liposomes (Ledley et al., *J. Pediatrics* I 10: 1, 1987); or in proteoliposomes that contain viral envelope receptor proteins (Nicolau et al., *Proc. Natl. Acad. Sci. U.S.A.* BD: 1068, 1983); and DNA coupled to a polylysine-glycoprotein carrier complex. In addition, "gene guns" have been used for gene delivery into cells (Australian Patent No. 9068389). Naked DNA, or DNA associated with liposomes, can be formulated in liquid carrier solutions for injection into interstitial spaces for transfer of DNA into cells (Felgner, WO90/11092).

Polynucleotide sequences encoding a TGF-α polypeptide or functional peptide fragment or mimetic, can be cloned into vectors suitable for delivery to host cells for expression. In particular retroviral vectors containing the polypeptides of the invention are particularly suitable for delivering polynucleotides to cells for gene therapy. Current strategies for gene therapy are reviewed in "The Development of Human Gene Therapy," Ed. Theodore Friedmann, Cold Spring Harbor Laboratory Press, New York, 1999, the disclosure of which is incorporated herein.

Delivery of a polynucleotide of interest may be accomplished in vivo by administration of the vectors to an individual subject, typically by systemic administration (e.g., intravenous, intraperitoneal, intramuscular, subdermal, or intracranial infusion). Alternatively, the vectors may be used to deliver polynucleotides to cells ex vivo such as cells explanted from an individual patient (e.g., tumor-infiltrating lymphocytes, bone marrow aspirates, tissue biopsy) or universal donor hematopoietic stem cells, followed by reimplantation of the cells into a patient, usually after selection for cells which have incorporated the polynucleotide.

Vectors comprising a trophic factor-encoding nucleic acid can be introduced into a variety of cells and tissues including myeloid cells, bone marrow cells, lymphocytes, hepatocytes, fibroblasts, lung cells, epithelial cells and muscle cells. For example, polynucleotides encoding a TGF-α polypeptide may be transferred to (introduced into) stem cells.

In another aspect, a trophic factor can delivered via a cell that has been genetically modified to express the trophic factor. Thus, the present invention also encompasses gene therapy methods wherein cells are used to introduce TGF-α into a subject such that the TGF-α is expressed. Such gene therapy methods may be used to treat and/or prevent conditions associated with neural degeneration. For example, a vector can be used to transfer a genetic element encoding a trophic factor, such as TGF-α, into a cell such that the cell is modified to express a TGF-α polypeptide beneficial to the treatment of a pathological disorder.

A "vector" refers to a recombinant DNA or RNA construct, such as a plasmid, a phage, recombinant virus, or other vector that, upon introduction into an appropriate host cell of the invention, results in a modification of a pre-mesenchymal, pre hematopoietic stem cell. Appropriate expression vectors are well known to those with ordinary skill in the art and include those that are replicable in eukaryotic and/or prokaryotic cells and those that remain episomal or those that integrate into the host cell genome.

Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing gene expression and function are known to those skilled in the art. Gene presence, amplification, and/or expression may be measured in a sample, directly, for example, by conventional Southern blotting, Northern blotting to quantitate the transcription of mRNA, dot blotting (DNA or RNA analysis), or in situ hybridization, using an appropriately labeled probe which may be based on a sequence provided herein. Those skilled in the art will readily envisage how these methods may be modified, if desired.

The invention provides a method of modulating progenitor cell proliferation, and/or migration, and/or differentiation by introducing an effective amount of a trophic factor into a subject such that progenitor cells are induced to proliferate, and/or migrate and/or differentiate at or into the site of neurological damage or injury. The present study indicates that peripheral administration of TGF-α provides an effective method for the treatment of a number of diseases and disorders associated neurological deficits.

Neurological deficits that are treated using the instant methods include degenerative diseases, such as Alzheimer's Disease (AD), Parkinson's Disease (PD), Amyotrophic lateral sclerosis (ALS), Huntington's Disease (HD), Pick's disease, progressive supranuclear palsy, striatonigral degeneration, cortico-basal degeneration, olivopontocerebellar atrophy, Leigh's disease, infantile necrotizing encephalomyelopathy, Hunter's disease, mucopolysaccharidosis, various leukodystrophies (such as Krabbe's disease, Pelizaeus-Merzbacher disease and the like), amaurotic (familial) idiocy, Kufs disease, Spielmayer-Vogt disease, Tay Sachs disease, Batten disease, Jansky-Bielschowsky disease, Reye's disease, cerebral ataxia, chronic alcoholism, beriberi, Hallervorden-Spatz; syndrome, cerebellar degeneration, and the like.

For example, dopaminergic cells are known to be lost in association with a number of debilitating neurodegenerative diseases such as Parkinson's disease. In the cerebral cortex, neurons and glia are lost following ischemic episodes caused by a thrombus or embolus. In the spinal cord, motor neurons are particularly susceptible to damage due to a traumatic injury. The tissue may be disrupted by physical force (e.g., ablating or excising neurons, or severing one or more of the processes that extend from the neuronal cell bodies) or by applying a chemical substance such as a toxin or neurotoxin (e.g., ricin or 6-OHDA), a corrosive chemical (e.g., an acidic or basic solution), a compound that induces apoptosis (see, e.g., Leavitt et al., Soc. Neurosci. Abstr. 22:505, 1996), a compound that induces demyelination (see, e.g., Lachapelle et al., Soc. Neurosci. Abstr. 23:1689, 1997), or a compound capable of inhibiting the activity of the cell, e.g., an antisense oligonucleotide (such as an oligonucleotide that inhibits transcription of the gene encoding the cell's primary neurotransmitter), an antibody, or a polypeptide. Many such compounds are known to those of ordinary skill in the art and include compounds that bind to, but fail to activate, a receptor on the cell surface, such as the metabotropic receptors normally bound by glutamate. Moreover, neural tissue may be disrupted by the administration of chemotherapeutic agents, such as radiation or chemical compositions, necessary to treat a neoplastic lesion of the CNS. Thus, the invention encompasses the peripheral administration of TGF-α prior to, during or subsequent to the administration of a chemotherapeutic agent to the CNS for the purpose of regenerating neural tissue damaged by a necessary medical treatment. The medical treatment can include, for example, surgical procedures that disrupt tissue of the CNS. For example, in the studies described below, the effect of dopaminergic neuron denervation with 6-OHDA, together with the peripheral administration of TGF-α, on neurogenesis is apparent.

Accordingly, in one embodiment, a TGF-α polypeptide, fragment or mimetic can be used to treat, repair or regenerate a tissue or a subject having a neurological injury. In one embodiment, the invention provides a continuous or intermittent infusion of a TGF-α polypeptide, a related polypeptide, mimetic, or functional fragment thereof having TGF-α activity peripheral to a site of injury or at a site that allows for delivery of the TGF-α polypeptide, fragment or mimetic to the site of injury (e.g., a vein or portal upstream of the injured site). The TGF-α polypeptide, a related polypeptide, mimetic, or functional fragment thereof having TGF-α activity of the invention delivered to the site of injury promotes the proliferation, and/or migration, and/or differentiation of progenitor cells that are located at the site of injury, or circulating in the lumen of a blood vessel near the site of injury, or are located in the wall of the blood vessel near the site of injury, and thus promotes tissue repair and regeneration.

In another embodiment, administration of a TGF-α polypeptide, a related polypeptide, mimetic, or functional fragment thereof having TGF-α activity to a subject peripheral to a site of injury or at a site that allows for delivery of the TGF-α polypeptide, fragment or mimetic to the site of injury (e.g., a vein or portal upstream of the injured site) and to the location of a progenitor cell capable of differentiating into a neuronal cell. For example, the invention provides a mechanism for inducing an endogenous progenitor cell to migrate and/or differentiate into a neuronal cell at a site of CNS damage. The progenitor cell can be, for example, a hematopoietic progenitor cell which is located at or near the site of CNS damage or is located distally from the site of damage. Such cells generally reside in bone marrow tissue, but can be circulating throughout the subject as well as stationary in a blood vessel at or near the site of injury or damage. Thus, the TGF-α polypeptide, a related polypeptide, TGF-α mimetic, or functional fragment thereof having TGF-α activity of the invention delivered to the site of injury promotes the proliferation, migration, and/or differentiation of progenitor cells that are located at the site of injury, or circulating in the lumen of a blood vessel near the site of injury, or are located in the wall of the blood vessel near the site of injury, and thus promotes tissue repair and regeneration.

Further, injuries (traumatic or neurotoxic) that cause a loss of neuronal function can be treated by the functional polypeptides and mimetics of the invention.

Reid et al. describes the continuous infusion of TGF-α into brain tissue following injury (see, WO 99/06060, and U.S. patent application Ser. No. 09/129,028 which are incorporated herein by reference in their entirety). The present invention describes methods whereby peripheral administration of a TGF-α polypeptide, a TGF-α related polypeptide, mimetic, or a fragment having TGF-α activity either before, prior to, simultaneous with or following tissue injury can stimulate progenitor cells at or near the damaged tissue or distal from the damaged or injured tissue to proliferate, migrate and differentiate to replace or repair cells at the site of injury and to ameliorate the effects of such damage.

The term "ameliorate" denotes a lessening of the detrimental effect of the disease-inducing response in the patient receiving therapy. The terms "treating," "treatment," and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

Generally, the terms "treating", "treatment" and the like are used herein to mean affecting a subject, tissue or cell to obtain a desired pharmacologic and/or physiologic effect. The effect may be prophylactic in terms of completely or partially preventing a disease or disorder or sign or symptom thereof, and/or may be therapeutic in terms of a partial or complete cure for a disorder or disease and/or adverse effect attributable to the disorder or disease. "Treating" as used herein covers any treatment of, or prevention of, or inhibition of a disorder or disease in a subject. The subject can be an invertebrate, a vertebrate, a mammal, and particularly a human, and includes by way of example: (a) preventing the disease or disorder from occurring in a subject that may be predisposed to the disease or disorder, but has not yet been diagnosed as having it; (b) inhibiting the disease or disorder, i.e., arresting its progression; or (c) relieving or ameliorating the disease or disorder, i.e., causing regression. Thus, treating as used herein includes, for example, repair and regeneration of damaged or injured tissue or cells at the site of injury or prophylactic treatments to prevent damage, e.g., before chemotherapy.

The present invention provides for peripheral administration of TGF-α polypeptide, a related polypeptide, a TGF-α mimetic, or a TGF-α functional fragment having TGF-α activity. Peripheral administration of TGFα can be as a single dose, or multiple doses, or continuous (e.g., continuous infusion). Multiple doses can be administered hourly, daily, weekly, or monthly, depending, in part, on the severity of the injury or damage, the response of the individual to treatment, etc.

A single, multiple, or continuous dose peripheral injection can be administered within minutes (e.g., within about 5 to about 120 minutes), within hours (e.g., within about 2 hours to about 36 hours), within days (e.g., within about 2 days to about 14 days), or within weeks (e.g. within about 2 weeks to about 8 weeks) after tissue damage or injury.

The administration of these compounds induces modulation of neural activity or neurogenesis, i.e., the administration modulates neurogenesis or neural activity. As used herein the term "modulating" or "modulation" including any change in neural activity or any neurogenesis, which includes, but is not limited to, differentiation (including re-differentiation or dedifferentiation), migration, and proliferation of neurons, neural stem cells or any other cell, including progenitor cells or stem cells.

In one aspect, the initial events in the modulation of neural activity or neurogenesis including migration and/or differentiation of cells to the CNS from an endothelium or from a perivascular cell in the CNS.

Alternatively, the initial events in the modulation of neural activity or neurogenesis including migration and/or differentiation of cells to the CNS from an non-CNS tissue compartment, such as the bone marrow, the blood, the spleen, a lymph node, and the like. Modulation of neural activity or neurogenesis can also include migration and/or differentiation of cells at a site of injury or damage in the CNS of a subject. The modulation includes, but is not limited to, progenitor cell (or progeny thereof) proliferation, migration, differentiation (including dedifferentiation or redifferentiation) of cells, including endogenous progenitor cells. Such cells can be located distally from the site of injury, such as in a vascular endothelium, perivascularly, or recruited to the CNS for any tissue or cell reservoir, such as the bone marrow or spleen. Alternatively, such cell can be located at or near the site of tissue injury.

Compositions (e.g., as a single unit dosage delivery) also can be administered immediately adjacent to the site of injury or can be, for example, to a vessel (blood or lymphatic) that drains or flows to the site of injury.

Methods of administration of the growth factor include, but are not limited to, subcutaneous, topical, oral, intradermal, intramuscular, intraperitoneal, intravascular (e.g., intravenous), subcutaneous, intranasal, and epidural routes. The cells of the invention may be administered by any convenient route, for example, by infusion or bolus injection, by absorption through epithelial or mucocutaneous linings (e.g., oral mucosa, rectal and intestinal mucosa, etc.), and may be administered together with other biologically active agents. Administration can be systemic or local.

In alternative aspects, the trophic factor is peripherally administered to a subject in need of such treatment by, for example and not by way of limitation, infusion during surgery, injection, a catheter means, or an implant means, the implant being of a porous, non-porous, or gelatinous material, including membranes, such as sialastic membranes, or fibers. Alternatively, a trophic factor can be included in a controlled release matrix which can be positioned in proximity to, but not in direct contact with, damaged neural tissue thereby promoting regeneration of such tissue. The term "controlled release matrix" means any composition that allows the slow release of a trophic factor which is mixed or admixed therein. The matrix can be a solid composition, a porous material, or a semi-solid, gel or liquid suspension containing bioactive substances.

Injuries treatable by the methods of the invention include, for example, gunshot wounds, injuries caused by blunt force, penetration injuries, injuries caused by surgical procedure (e.g., tumor removal, abscess removal, epilepsy lesion removal) poisoning (e.g., carbon monoxide), shaken baby syndrome, adverse reactions to medications, drug overdoses, and post-traumatic encephalopathy. Ischemia can further cause CNS injury due to disruption of blood flow or oxygen delivery that can kill or injure neurons and glial cells. Such injuries can be treated by administration of the TGF-α functional polypeptides and include, for example, injuries caused by stroke, anoxia, hypoxia, partial drowning, myoclomis, severe smoke inhalation, dystonias, and acquired hydrocephalus. Developmental disorders that can be treated by the functional peptides include, for example, schizophrenia, certain forms of severe mental retardation, cerebral palsey, congenital hydrocephalus, severe autism, Downs Syndrome, LHRH/hypothalamic disorder, and spina bifida. The method can be further used to treat disorders affecting vision caused by the loss or failure of retinal cells and include, for example, diabetic retinopathy, serious retinal detachment (associated with glaucoma), traumatic injury to the retina, retinal vascular occlusion, macular degeneration, optic nerve atrophy and other retinal degenerative diseases. For example, Young et al. (Mol. Cell. Neurosciences 16:197, 2000) have found that adult neural stem cells may be useful in treating blindness due to degradation of the retinas.

Injuries to the spinal cord and associated ganglia can be treated by the methods of the invention. Examples of spinal cord injuries are post-polio syndrome, amyotrophic lateral sclerosis (ALS), traumatic injury, surgical injury, and paralytic diseases. Demyelinating autoimmune disorders can be treated by administration of the functional peptides and include, for example, multiple sclerosis. The functional peptides can also be used to treat neurological deficits caused by infection of inflammatory diseases, including, for example, Creutzfeldt-Jacob disease and other slow virus infectious diseases of the CNS, AIDS encephalopathy, post-encephalitic Parkinsonism, viral encephalitis, bacterial meningitis and other CNS effects of infectious diseases.

The invention includes various pharmaceutical compositions useful for delivery or administration of a polypeptide, peptide or mimetic useful in the method of the invention. In one embodiment, the pharmaceutical compositions are useful in managing or treating neuronal tissue damage and cell renewal in a subject. The pharmaceutical compositions according to the invention are prepared by bringing a polypeptide or peptide derivative of TGF-α, a TGF-α mimetic into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases.

Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

In some embodiments, pharmaceutical compositions are prepared and administered in dose units. Solid dose units are tablets, capsules and suppositories and including, for example, alginate based pH dependent release gel caps. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or by several smaller dose units and also by multiple administrations of subdivided doses at specific intervals.

The pharmaceutical compositions according to the invention may be administered systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference. As used herein, a "therapeutically effective" amount of a composition containing a trophic factor that promotes neural regeneration is an amount that is effective in inducing the proliferation, migration, or differentiation of a progenitor cell, or progeny thereof, at or into a site of injury or damage in the central nervous system of the subject, subsequent to peripheral administration of the trophic factor. The term "induce" or "induction" as used herein, refers to the activation, stimulation, enhancement, initiation and or maintenance of the cellular mechanisms or processes necessary for the formation of any of the tissue, repair process or development as described herein.

The invention provides a pharmaceutical composition useful for administering a TGF-α polypeptide or functional fragment, or a nucleic acid encoding a TGF-α polypeptide or functional fragment, to a subject in need of such treatment. "Administering" the pharmaceutical composition of the invention may be accomplished by any means known to the skilled artisan. A "subject" refers to a mammal, e.g., a human.

The TGF-α polypeptide or functional fragment can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate.

Carriers for occlusive dressings can be used to increase skin permeability and enhance absorption. Liquid dosage forms for oral administration may generally comprise a liposome solution containing the liquid dosage form. Suitable solid or liquid pharmaceutical preparation forms are, for example, granules, powders, tablets, coated tablets, microcapsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

Sterile injectable solutions can be prepared by incorporating the active agent (e.g., TGF-α) in the required amount (e.g., about 10 µg to about 10 mg/kg) in an appropriate solvent and then sterilizing, such as by sterile filtration. Further, powders can be prepared by standard techniques such as freeze-drying or vacuum drying.

In another embodiment, the active agent is prepared with a biodegradable carrier for sustained release characteristics for either sustained release in the subject or target organ by implantation with long-term active agent release characteristics to the intended site of activity. Biodegradable polymers include, for example, ethylene vinyl acetate, polyanhydrides, polyglycolic acids, polylactic acids, collagen, polyorthoesters, and poly acetic acid. Liposomal formulation can also be used.

Kits

The invention provides kits that contain the pharmaceutical compositions comprising a trophic factor, for use in carrying out the instant methods. The kit can contain instructional material teaching methodologies, e.g., methods for peripherally administer a TGF-α polypeptide, a TGF-α related polypeptide, a TGF-α functional fragment, or a TGF-α mimetic formulation. Kits containing pharmaceutical preparations can include directions as to indications, dosages, routes and methods of administration, and the like.

It must be noted that as used herein and in the appended claims, the singular forms "a," "and," and "the" include plural referents, unless the context clearly dictates otherwise. Thus, for example, reference to "a target cell" includes a plurality of such cells, and reference to "the expression vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Any methods, cells and genes similar or equivalent to those described herein can be used in the practice or testing of the invention.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLES

The following example is offered to illustrate, but not to limit the claimed invention.

Example 1

This example demonstrates that the methods of the invention are effective for generating differentiated neurons in a site of injury in the central nervous system after peripheral administration, in this example, subcutaneous administration, of a tropic factor, in this example, the exemplary TGF-α.

Materials and Methods

The hemiparkinsonian rat model was utilized to simulate damage or injury in the CNS. 240-260 g adult male Sprague Dawley rats (Simonsen Labs) were used throughout the experiments. Briefly, acute lesions of the left substantia nigra (SN) were induced by stereotaxic injection of 6-OHDA into the dorsal-rostral SN at predetermined coordinates. Immediately following this surgery, an osmotic minipump (model 2004—Durect Corp., Palo Alto, Calif.) containing either 100 mg TGF-alpha (R&D Systems, Minneapolis, Minn.) in 200 ml artificial cerebrospinal fluid (aCSF)(n=5) or 200 ml aCSF alone (n=5) was placed subcutaneously in the intrascapular area. The pumps delivered solution for 28 days, providing TGF-α at a dose of 3 mg/day in the experimental group. 5'-Bromo-2-deoxyuridine (BrdU-La Roche, Atlanta, Ga.) was given as a single daily intraperitoneal injection (50 mg/Kg) for the next seven days.

turning behavior throughout the study (n=1 in the TGF-α group) were presumed to have had a failed lesion and were excluded from the analysis. The data show that in the first six weeks post-lesion there is no statistically significant difference between the TGF-α infused animals and controls, or within each group over the six weeks. Between weeks 6 and 10, however, the TGF-α infused animals show a uniform reduction in the turning behavior by approximately 40% of the preceding levels at weeks 1-6, whereas the controls show no such reduction. The difference between the groups is statistically significant ($p=0.048$), more so ($p=0.01$) if the animals that have erratic behavior in the course of the study are excluded from the analysis (animal #3 TGF-α group, animal #4 aCSF group—Table 1).

TABLE 1

| Animal | Week 1 | 2 | 3 | 4 | 6 | 10 | Mean wk 1-6 | wk 10 | % change |
|---|---|---|---|---|---|---|---|---|---|
| TGF-α infused animals | | | | | | | | | |
| 1 | 230 | 260 | 248 | 268 | 296 | 188 | 260.4 | 188 | −27.8 |
| 2 | 240 | 468 | 300 | 181 | 272 | 148 | 292.2 | 148 | −49.3 |
| 3 | 0 | 0 | 148 | 64 | 222 | 84 | 86.8 | 84 | −3.2 |
| 4 | 244 | 196 | 276 | 224 | 232 | 96 | 234.4 | 96 | −59 |
| Mean | 178.5 | 231 | 243 | 184.25 | 255.5 | 129 | 218.45 | 129 | −40.9 |
| Std. Dev. | 119.1 | 192.9 | 66.8 | 87.7 | 34.6 | 48.2 | 78.7 | 41.7 | 24.8 |
| aCSF infused animals | | | | | | | | | |
| 1 | 254 | 322 | 272 | 324 | 368 | 340 | 308 | 340 | 10.4 |
| 2 | 228 | 308 | 304 | 308 | 304 | 281 | 290.4 | 281 | −3.2 |
| 3 | 160 | 600 | 160 | 296 | 224 | 200 | 288 | 200 | −30.6 |
| 4 | 0 | 28 | 0 | 322 | 112 | 108 | 92.4 | 108 | 16.9 |
| 5 | 228 | 292 | 328 | 136 | 254 | 310 | 247.6 | 310 | 25.2 |
| Mean | 174 | 310 | 212.8 | 277.2 | 252.4 | 247.8 | 245.28 | 247.8 | 1 |
| Std. Dev. | 103.3 | 202.5 | 135.2 | 79.7 | 95.6 | 93.9 | 123.3 | 121.41 | 120.3 |
| test (two tailed, unequal variance) p = 0.048* | | | | | | 0.049 | | | |

Apomorphine-induced turning behavior was assessed as described at 1, 2, 3, 4, 6 and 10 weeks after the SN lesion and pump placement. Animals were sacrificed at 10 weeks post-lesion by intracardiac perfusion of 0.9% saline/4% paraformaldehyde.

Brains were sectioned at 40 mm on a freezing microtome and processed for single and double immunoperoxidase and immunofluorescence staining, as previously described (Fallon et al., 2000) using primary antibodies to BrdU (mouse anti—1:400, Chemicon, Temecula, Calif.; rat anti—1:400, Harlan, Raleigh, N.C.), tyrosine hydroxylase (rabbit anti—, 1:1000-1:2000, Protos Biotech, NY, N.Y.), dopamine transporter (DAT, rat anti—, 1:1000, Chemicon, Temecula, Calif.), some markers for early stages of neuronal differentiation: b-III tubulin (rabbit anti—1:1000, mouse anti—1:500, Research Diagnostics, Flanders, N.J.), CD 24 (rat anti—Serotec, Raleigh, N.C.), doublecortin (DCX, mouse anti—, 1:250) the astrocytic marker glial fibrillary acidic protein (GFAP, rabbit anti—, 1:400, Dako, Carpinteria, Calif.), a marker for activated microglia 1 A-I (clone OX-6, mouse anti—, 1:100, Serotec, Raleigh, N.C.) and additionally for a marker of primitive HSCs-CD34 (rat anti—, 1:50, BDPharmingen, San Diego, Calif.) Highly species cross-adsorbed biotinylated (Vector Labs., Burlingame, Calif.) or fluorescent (Molecular Probes, Eugene, Oreg.) secondary antibodies were used for visualization as previously described (Fallon et al., 2000).

Results

The turning behavior of the test and control groups over the 10-week period is shown in Table 1. Animals that showed no FIGS. 1i and 1ii provide data for rotational behavior of 24 individual animals receiving TGF-α (n=12) or controls (n=12) over a fifteen-week study period. The values are the total number of contralateral rotations counted in 30 min. The p value (two-tailed, equal variance) is computed on a weekly basis. The results show that animals receiving TGF-α show progressively fewer mean rotations than the control group from week 6. At week 15 post-lesion the TGF-α group shows 20% fewer rotations than the control group ($p=0.0364$) (see Table 2). FIG. 2 is a graph of data showing mean rotations for TGF-α-treated animals and controls, spanning a fifteen-week time period. The data are the behavioral data for 24 animals receiving subcutaneous TGF-α and controls followed for 15 weeks. The data indicate that animals receiving subcutaneous TGF-α show a 20% reduction in motor deficits ($p=0.0364$) when compared to controls at week 15 post-infusion.

Histomorphology

Brain sections were analyzed from the rostral forebrain to the midbrain. In the rostral forebrain of TGF-α infused animals, cells expressing CD24 and DCX, markers for neurons in early stages of differentiation, were identified in the hemisphere ipsilateral to the SN lesion in the anterior cingulate cortex (as well as contralateral hemisphere), dorsolateral to mid-striatum, the dorsal Islands of Calleja complex and piriform cortex, as well as the septum and the area surrounding the organum vasculosum lamina terminalis. $CD24^+$ and $DCX^+$ are also located in the deep layers of the dorsal frontal and parietal cortices, along the deep cortical layer VIb and adjacent external capsule and in both the dorsolateral and ventromedial SVZs bilaterally. Scattered clusters of cells in all these areas (except the SVZ) are also TH$^+$, and discrete TH$^+$ axons are seen radiating radially from the cell bodies, in the coronal plane, in the dorsolateral striatum, in contrast to their usual rostro-caudal orientation through the striatum. Increased BrdU staining is also seen in these areas as compared to the rest of the forebrain, especially in the ipsilateral striatum. Control animals do not show an increase in new cells in the striatum. Double labeling studies reveal most of the BrdU positive cells to be microglia (OX6$^+$).

Subsets of these cells are also positive for CD34$^+$ and show a well-differentiated morphology typical of neurons with somata, axons and dendrites. Cells of the SVZ, some cells of the olfactory bulb and hippocampus, are also CD34$^+$. CD34$^+$ is a marker normally expressed on primitive HSCs. There is considerable overlap of the distribution of cells immunoreactive for the neuronal and hematopoietic markers and, in addition, these areas overlap the normal DA innervation of the forebrain: Except for the cells described in the areas above, none of the neurons in the areas of the brain not receiving an input from the ipsilateral nigrostriatal or mesocortical projections are positive for DCX, CD24 or CD34.

CD24$^+$, DCX$^+$ or CD34$^+$ cells are not present in the contralateral hemisphere except for the cingulate cortex and SVZ. Occasional BrdU$^+$ cells are seen scattered through the contralateral hemisphere without any localized areas of increased cell numbers.

In all areas examined no β-III tubulin+cells are seen as would be expected. In control animals no cells stain positive for CD24, β-III tubulin or CD34 in either hemisphere, except for cells in the SVZ, some of which are BrdU$^+$ and CD34$^+$. Few BrdU+ cells are seen scattered uniformly throughout the section without any areas of localized aggregation. Some cells in the ventral forebrain (Islands of Calleja and piriform cortex) are CD34$^+$ and are located either within blood vessels, or in the immediate perivascular space.

A further specific characteristic of the distribution of many of the immunoreactive cells described above is their aggregation in the vicinity around blood vessels. This pattern is most conspicuous in the dorsolateral striatum, and is also observed in the dorsal Islands of Calleja complex and portions of the frontal/parietal cortex. In more caudal sections of the forebrain cells with immunoreactivity similar to that described above are seen primarily ipsilateral to the lesioned nigrostriatal pathway, in the lateral striatum (and a few in the cortex overlying it), the periventricular areas and lateral hypothalamus.

In the midbrain numerous BrdU$^+$ cells are seen distributed along the needle tract and along the lesioned SN compacta and extending ventrally through the SN reticulata in both the TGF-α infused and control animals. In TGF-α infused group a small number of TH$^+$ and DAT$^+$ cells are seen in the area. The TH$^+$ or DAT$^+$ cells have an irregular spherical soma with small fibers radiating from them, although a few have an inverted pyramidal morphology. Some of the cells are also CD34$^+$. These TH4$^+$ and co-distributed DAT$^+$ cells align along a vascular invagination of the pia-arachnoid from the ventral surface of the midbrain. The vast majority of the BrdU$^+$ cells, in both the test and control animals, co-localize either GFAP or 1A-I (clone OX-6), indicating they are newly generated astrocytes and microglia.

Following a unilateral lesion of the nigrostriatal pathway, animals received subcutaneous TGF-α for four weeks and were tested for turning behavior for a total of ten weeks. Animals were sacrificed at ten weeks and brains processed for evidence of generation of new neural precursors, mature neurons and fully differentiated phenotypes, and additionally for hematopoietic stem cell (HSC) antigens. A 40% reduction in motor deficits in the TGF-α-infused animals ten weeks after the lesion was identified. Analysis of the brains of TGF-α-infused animals reveal the presence of recently generated neurons in multiple areas of the forebrain and midbrain, some of which show terminal differentiation into dopamine (DA) producing neurons. The present study demonstrates the presence of newly generated differentiated neurons expressing antigens normally expressed in progenitor cells derived from endothelial cells, perivascular cells, circulating HSCs and/or SVZ progenitor cells. These data indicate that peripherally administered TGF-α may induce functional recovery from CNS damage through in vivo mechanisms that include mobilization of progenitor cells into areas of the brain that are acutely denervated, and their differentiation into functional neurons resulting in a reduction of the motor deficits induced in this animal model.

Peripheral infusions of TGF-α started at the time of injury, induce neurogenesis in multiple areas of the lesioned brain, as evidenced by the presence of CD24$^+$ and DCX$^+$ cells. β-III tubulin is transiently expressed in developing neurons at an early stage of differentiation. The absence of β-III tubulin$^+$ cells indicates that at the time point when the brains are examined (week 10) the majority of newly generated neurons are at a more mature stage of differentiation. While numerous cells are positive for CD24 and DCX markers through the rostral-caudal extent of the forebrain, only a subset of these cells double-stain for BrdU. This data indicates that such neurons are generated beyond the first week, the period when BrdU is administered. In contrast, intrastriatal infusions of TGF-α following the same injury paradigm induce a rapid proliferation during the first week. The difference in response time indicates that additional mechanisms are in operation for TGF-α arriving at the CNS intravascularly than when given parenchymally.

The response observed in the SN appears to be predominantly an acute inflammatory response to the 6-OHDA lesion. The prominent BrdU+/GFAP+ and BrdU+/1A-1+ (OX6) co-localization observed imply that florid astrogliosis and microgliosis occur in the SN during the first week when BrdU is administered. The few newly formed TH+/DAT+cells seen can be viewed as serving to replace disrupted DA circuits within the SN. Neurons of the SN pars reticulata are relatively spared from the 6-OHDA lesion, and are known to receive afferents from the SN pars compacta. It is conceivable that the SN pars reticulata neurons respond to denervation as described above in the forebrain. The newly generated neurons in the SN are also spatially related to a vascular core, a ventromedial sulcus in the midbrain.

A further conclusion from this study is that the loss of a specific afferent input in an area of the CNS results in a response, within the denervated areas, that directs the direction of differentiation of stem cells to replace the specific input lost. The present study shows that new DA neurons are generated in all areas denervated of DA inputs, including both the nigrostriatal and mesolimbocortical projection fields. The mesolimbocortical fibers project bilaterally to the frontal cortex and send ipsilateral projections to the lateral septum, and comprise both DA and non-DA neurons, both of which are interrupted by the midbrain 6-OHDA lesions.

The present study demonstrates that peripherally administered TGF-α is effective in inducing neurogenesis in multiple areas of the brain that have suffered injury or damage. The present study further demonstrates that neurogenesis resulting in the appearance of functional neurons and the reduction of motor impairment in mammals can modulated by the proliferation, migration, and/or differentiation of cerebral capillary endothelial cells, perivascular cells, circulating HSCs and/or SVZ progenitor cells.

A number of embodiments of the invention have been described. Nevertheless, it will be understood that various modifications may be made without departing from the spirit and scope of the invention. Accordingly, other embodiments are within the scope of the following claims.

What is claimed is:

1. A method of inducing migration of a progenitor cell or a progeny thereof to a site of neurological injury or damage in the central nervous system of a subject having neurological injury or damage, comprising:
   (a) administering a composition comprising a therapeutically effective amount of an exogenous TGF-α polypeptide to the subject, wherein the administration is parenteral, at an administration site outside the central nervous system and remote from the site of neurological injury or damage;
   (b) inducing proliferation of the progenitor cell or a progeny thereof to obtain proliferated cells;
   (c) inducing directed migration of proliferated cells to the site of neurological injury or damage; and
   (d) obtaining neurogenesis of functional neurons at or near the site of injury or damage, all of steps (b), (c) and (d) being evidenced by an amelioration of behavioral effects attributable to the injury or damage.

2. The method of claim 1, wherein the administration induces proliferation of the progenitor cell, or progeny thereof, at or near the site of injury or damage.

3. The method of claim 1, wherein the administration induces differentiation of the progenitor cell, or progeny thereof.

4. The method of claim 1, wherein the injury or damage results from a neurodegenerative disease.

5. The method of claim 4, wherein the neurodegenerative disease is Parkinson's disease.

6. The method of claim 1, wherein the administration is subcutaneous.

7. The method of claim 1, wherein the administration comprises introducing the composition comprising the exogenous TGF-α polypeptide into a lumen of a blood vessel.

8. The method of claim 1, wherein the administration comprises introducing the composition comprising the exogenous TGF-α polypeptide into a lumen of a lymph vessel.

9. A method of inducing migration of a progenitor cell or a progeny thereof to a site of neurological injury or damage in the central nervous system of a subject having neurological injury or damage, comprising:
   (a) administering a composition comprising a therapeutically effective amount of an exogenous TGF-α polypeptide into an administration site that is in a lumen of a blood vessel located outside the central nervous system of the subject;
   (b) inducing proliferation of the progenitor cell or a progeny thereof from the ependymal zone to obtain proliferated cells;
   (c) inducing directed migration of proliferated cells to the site of neurological injury or damage; and
   (d) obtaining neurogenesis of functional neurons at or near the site of injury or damage, all of steps (b), (c) and (d) being evidenced by an amelioration of behavioral effects attributable to the injury or damage.

10. A method of inducing migration of a progenitor cell or a progeny thereof to a site of neurological injury or damage in the central nervous system of a subject having neurological injury or damage, comprising:
    (a) administering a composition comprising a therapeutically effective amount of an exogenous TGF-α polypeptide to the subjects wherein said administration is intranasal or subcutaneous, at an administration site outside the central nervous system and remote from the site of neurological injury or damage;
    (b) permitting proliferation of the progenitor cell or a progeny thereof to obtain proliferated cells; permitting proliferated cells to migrate to and be present at the site of injury or damage; and
    (c) obtaining neurogenesis of functional neurons at or near the site of injury or damage, both of steps (b) and (c) being evidenced by an amelioration of behavioral effects attributable to the injury or damage.

11. A method of inducing migration of a progenitor cell or a progeny thereof to a site of neurological injury or damage in the central nervous system of a subject having neurological injury or damage, comprising:
    (a) administering a composition comprising a therapeutically effective amount of an exogenous TGF-α polypeptide to the subject wherein said administration is intranasal at an administration site outside the central nervous system and remote from the site of neurological injury or damage;
    (b) inducing proliferation of the progenitor cell or a progeny thereof to obtain proliferated cells;
    (c) inducing directed migration of proliferated cells to the site of neurological injury or damage; and
    (d) obtaining neurogenesis of functional neurons at or near the site of injury or damage, all of steps (b), (c) and (d) being evidenced by an amelioration of behavioral effects attributable to the injury or damage.

12. A method of inducing migration of a progenitor cell or a progeny thereof to a site of neurological injury or damage in the central nervous system of a subject having neurological injury or damage, comprising:
    (a) administering a composition comprising a therapeutically effective amount of an exogenous TGF-α polypeptide to the subject, wherein the administration is intranasal or subcutaneous, at an administration site outside the central nervous system and remote from the site of neurological injury or damage;
    (b) inducing proliferation of the progenitor cell or a progeny thereof to obtain proliferated cells;
    (c) inducing mass, directed migration of proliferated cells to the site of neurological injury or damage;
    (d) obtaining neurogenesis of functional neurons at or near the site of injury or damage; and
    (e) determining the presence of functioning neurons, all of steps (b), (c), (d) and (e) being evidenced by an amelioration of behavioral effects attributable to the injury or damage.

13. The method of any of claims 1, 9 or 10-12 wherein the progenitor cell or a progeny thereof is from the ependymal zone.

14. The method of any one of claims 1, 9, 10, or 12 wherein the administration is intranasal.

15. The method of any one of claims 1, 9 or 10-12 wherein the administration is over twenty-eight days.

16. The method of any one of claims 1, 9 or 10-12 wherein the administration is within weeks after the injury.

* * * * *